(12) United States Patent
Ikeda et al.

(10) Patent No.: US 11,301,964 B2
(45) Date of Patent: Apr. 12, 2022

(54) IMAGE PROCESSING APPARATUS, IMAGE PROCESSING METHOD, AND MEDICAL SYSTEM TO CORRECT BLURRING WITHOUT REMOVING A SCREEN MOTION CAUSED BY A BIOLOGICAL BODY MOTION

(71) Applicant: SONY CORPORATION, Tokyo (JP)

(72) Inventors: Kenji Ikeda, Kanagawa (JP); Hiroshi Ichiki, Kanagawa (JP); Hisakazu Shiraki, Kanagawa (JP); Daisuke Tsuru, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/086,269

(22) PCT Filed: Feb. 7, 2017

(86) PCT No.: PCT/JP2017/004432
§ 371 (c)(1),
(2) Date: Sep. 18, 2018

(87) PCT Pub. No.: WO2017/169139
PCT Pub. Date: Oct. 5, 2017

(65) Prior Publication Data
US 2020/0294203 A1    Sep. 17, 2020

(30) Foreign Application Priority Data
Mar. 29, 2016 (JP) .............................. JP2016-065219

(51) Int. Cl.
*G06T 5/00* (2006.01)
*G06T 7/246* (2017.01)
(Continued)

(52) U.S. Cl.
CPC .......... *G06T 5/003* (2013.01); *A61B 1/00009* (2013.01); *A61B 1/00188* (2013.01);
(Continued)

(58) Field of Classification Search
None
See application file for complete search history.

(56) References Cited

U.S. PATENT DOCUMENTS 6,842,196 B1    1/2005  Swift et al.
8,860,793 B2 *  10/2014 Lo .......................... G03B 15/05
                                                    348/68
(Continued)

FOREIGN PATENT DOCUMENTS

CN      103947184 A    7/2014
EP        2592824 A2   5/2013
(Continued)

OTHER PUBLICATIONS

Jager, Florian, and Joachim Hornegger. "Nonrigid registration of joint histograms for intensity standardization in magnetic resonace imaging." IEEE Transactions on Medical Imaging 28.1 (2008): 137-150 (Year: 2008).*

(Continued)

*Primary Examiner* — Tahmina N Ansari
(74) *Attorney, Agent, or Firm* — Chip Law Group

(57) ABSTRACT

To correct blurring without removing a screen motion caused by a biological body motion. [Solution] An image processing apparatus includes: a blurring amount estimation unit configured to estimate a blurring amount of a medical image including a biological body motion of a subject; and a blurring correction processing unit configured to perform blurring correction processing so as not to remove a screen motion caused by the biological body motion, on a basis of the blurring amount. This configuration makes it possible to (Continued)

correct blurring without removing a screen motion caused by a biological body motion. Thus, an optimum image for observing a biological body motion can be obtained.

19 Claims, 21 Drawing Sheets

(51) Int. Cl.
  *A61B 1/00* (2006.01)
  *G06T 5/20* (2006.01)
(52) U.S. Cl.
  CPC ............ *A61B 1/00193* (2013.01); *G06T 5/20* (2013.01); *G06T 7/246* (2017.01); *G06T 2207/10012* (2013.01); *G06T 2207/10056* (2013.01); *G06T 2207/10068* (2013.01); *G06T 2207/20201* (2013.01); *G06T 2207/30096* (2013.01)

(56) References Cited

U.S. PATENT DOCUMENTS

| | | | |
|---|---|---|---|
| 2010/0208944 A1* | 8/2010 | Fukunishi | H04N 5/23229 382/107 |
| 2012/0092472 A1 | 4/2012 | Higuchi | |
| 2012/0262559 A1* | 10/2012 | On | H04N 5/23267 348/65 |
| 2012/0263363 A1* | 10/2012 | Abboud | A61B 6/466 382/131 |
| 2013/0120601 A1 | 5/2013 | Han | |

FOREIGN PATENT DOCUMENTS

| | | | |
|---|---|---|---|
| JP | 05-049599 A | 3/1993 | |
| JP | 05-49599 A | 3/1993 | |
| JP | 2003-534837 A | 11/2003 | |
| JP | 2004-229002 A | 8/2004 | |
| JP | 2007-150445 A | 6/2007 | |
| JP | 2007-158853 A | 6/2007 | |
| JP | 2008-172309 A | 7/2008 | |
| JP | 2009-265179 A | 11/2009 | |
| JP | 2009-273577 A | 11/2009 | |
| JP | 2009-285132 A | 12/2009 | |
| JP | 2010-512173 A | 4/2010 | |
| JP | 2010-187347 A | 8/2010 | |
| JP | 2010-187723 A | 9/2010 | |
| JP | 2012-085696 A | 5/2012 | |
| JP | 2012-088466 A | 5/2012 | |
| JP | 2012-217579 A | 11/2012 | |
| JP | 2012-239644 A | 12/2012 | |
| JP | 2013-017752 A | 1/2013 | |
| JP | 5179398 B2 | 4/2013 | |
| JP | 2014-128015 A | 7/2014 | |
| JP | 2015-222925 A | 12/2015 | |
| JP | 2016-000065 A | 1/2016 | |
| KR | 10-2006-0099351 A | 9/2006 | |
| KR | 10-2013-0052994 A | 5/2013 | |
| WO | 2001/75798 A2 | 10/2001 | |
| WO | 2013/073757 A1 | 5/2013 | |
| WO | 2015/190319 A1 | 12/2015 | |

OTHER PUBLICATIONS

Machine Translation of JP 2010512173, machine translation obtained via Japanese Platform for Patent Information dated Jul. 26, 2021. (Year: 2010).*

Office Action for JP Patent Application No. 2018-508501 dated Nov. 10, 2020, 04 pages of Office Action and 04 pages of English Translation.

International Search Report and Written Opinion of PCT Application No. PCT/JP2017/004432, dated Apr. 18, 2017, 10 pages.

Partial European Search Report of EP Patent Application No. 17773687.3, dated Mar. 6, 2019, 28 pages.

Extended European Search Report of EP Patent Application No. 17773687.3, dated Jun. 12, 2019, 11 pages.

Office Action for JP Patent Application No. 2018-508501 dated Feb. 9, 2021, 05 pages of Office Action and 05 pages of English Translation.

Office Action for JP Patent Application No. 2018-508501, dated May 18, 2021, 07 pages of English Translation and 08 pages of Office Action.

Office Action for JP Patent Application No. 2018-508501, dated Oct. 12, 2021, 09 pages of English Translation and 09 pages of Office Action.

* cited by examiner

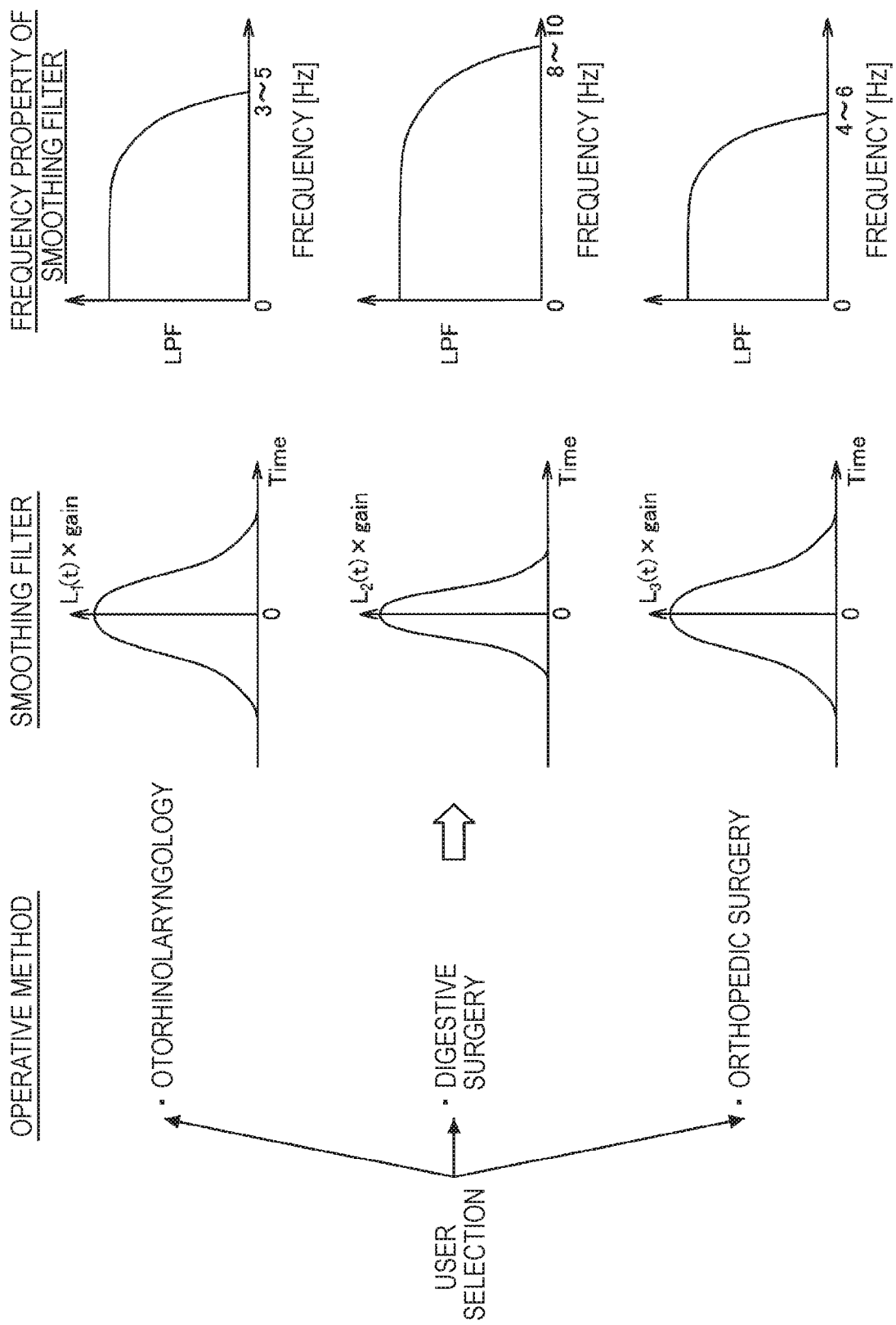

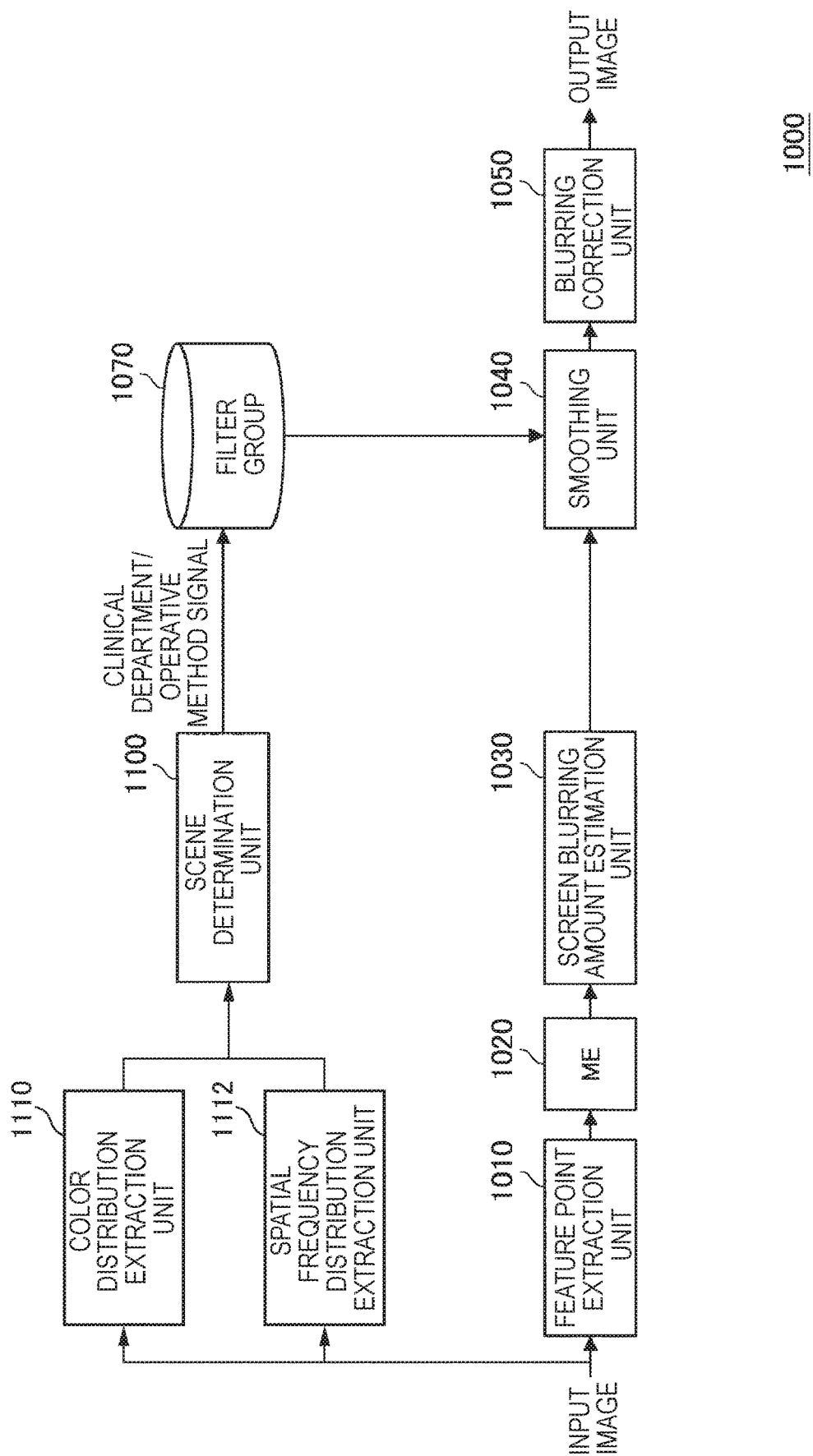

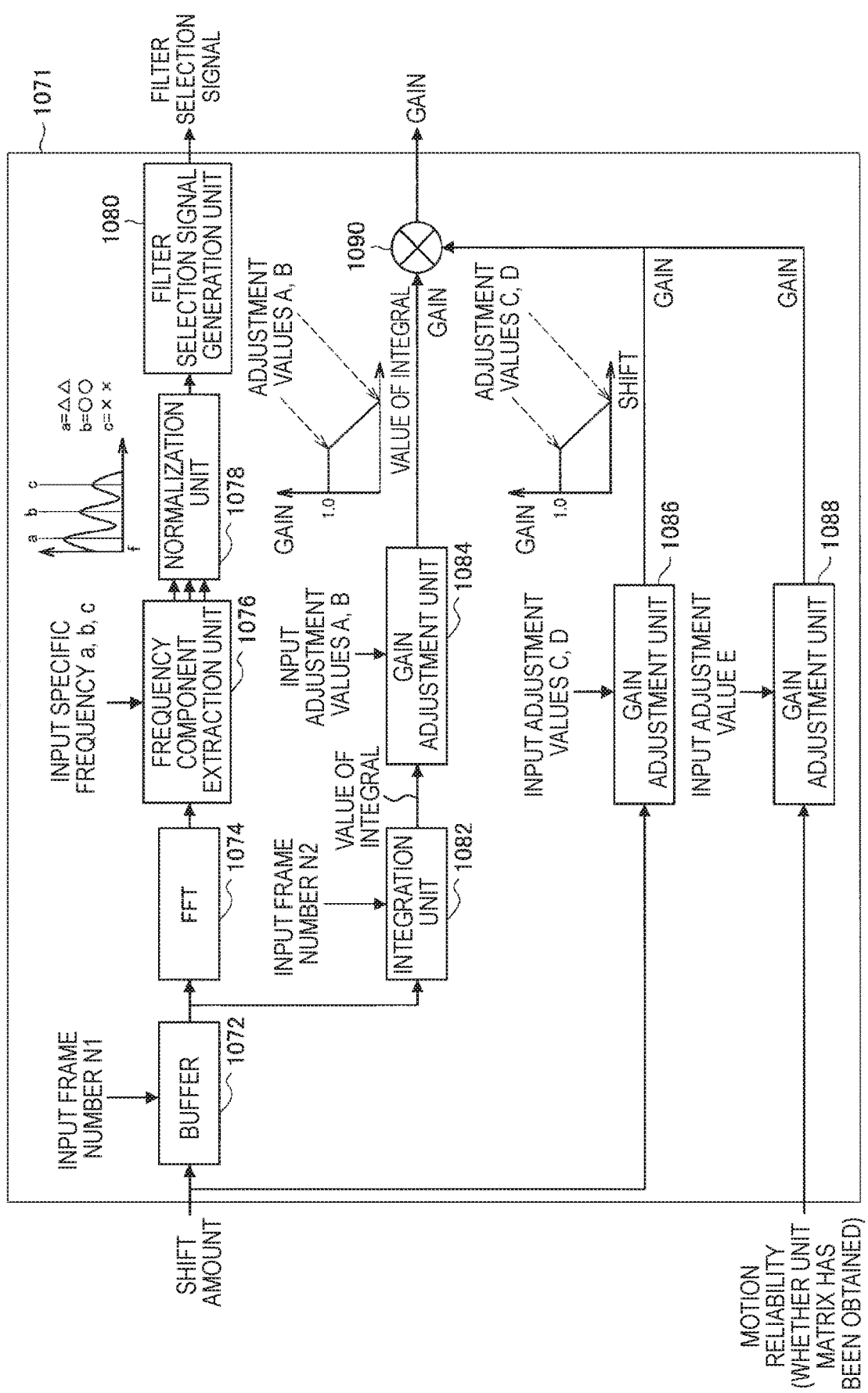

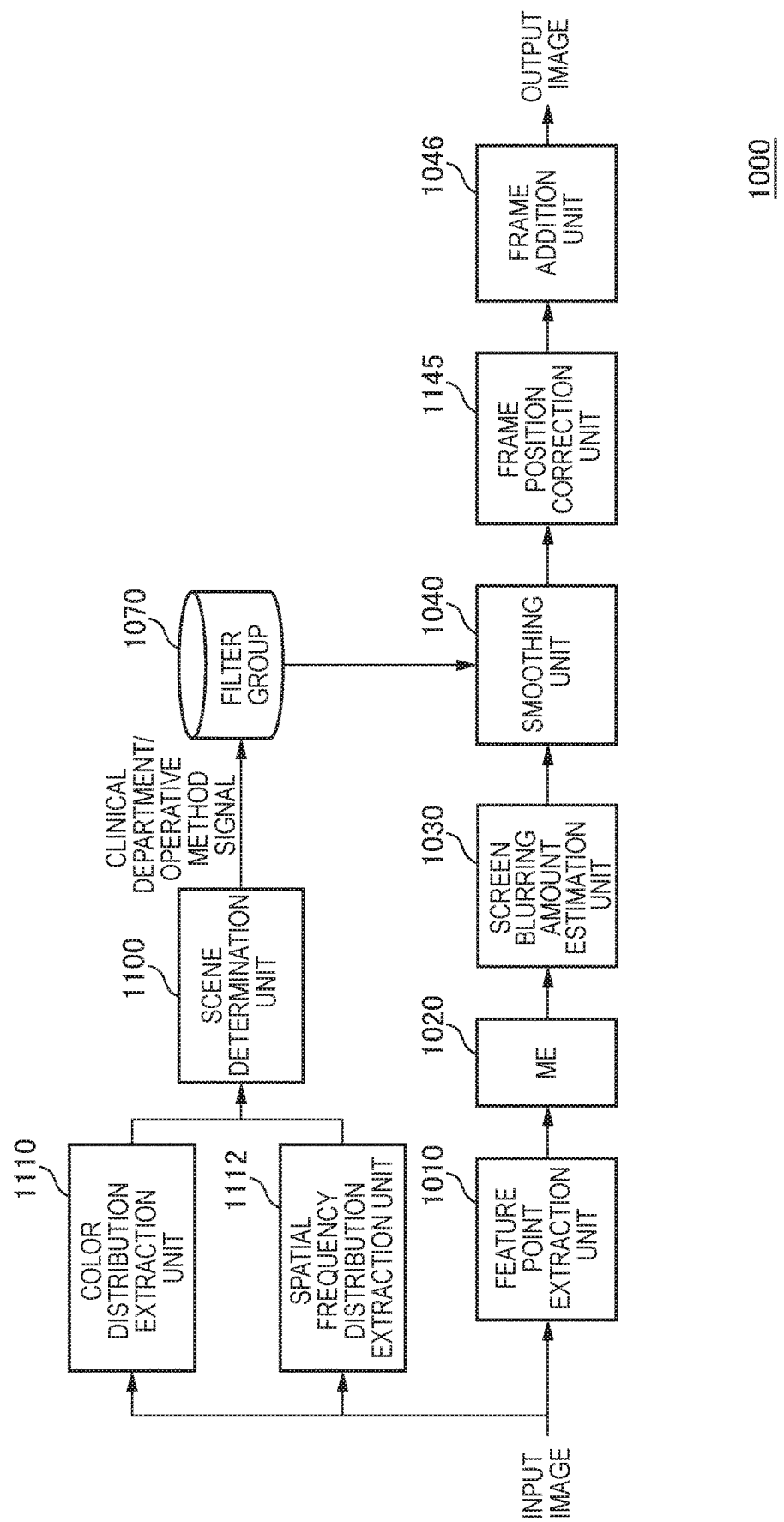

IMAGE PROCESSING APPARATUS, IMAGE PROCESSING METHOD, AND MEDICAL SYSTEM TO CORRECT BLURRING WITHOUT REMOVING A SCREEN MOTION CAUSED BY A BIOLOGICAL BODY MOTION

CROSS REFERENCE TO RELATED APPLICATIONS

This application is a U.S. National Phase of International Patent Application No. PCT/JP2017/004432 filed on Feb. 7, 2017, which claims priority benefit of Japanese Patent Application No. JP 2016-065219 filed in the Japan Patent Office on Mar. 29, 2016. Each of the above-referenced applications is hereby incorporated herein by reference in its entirety.

TECHNICAL FIELD

The present disclosure relates to an image processing apparatus, an image processing method, and a medical system.

BACKGROUND ART

Conventionally, for example, Patent Literature described below describes a technology that assumes setting the strength of a correction degree of a position shift on the basis of manipulation situation information indicating a situation of an endoscopic device, and presenting, to a user, a moving image with moderately-suppressed blurring.

CITATION LIST

Patent Literature

Patent Literature 1: JP 2012-85696A

DISCLOSURE OF INVENTION

Technical Problem

When a medical image is acquired by manipulating a medical device such as an endoscope, image burring corresponding to the manipulation of an operator is generated in some cases. On the other hand, in a medical image, due to the characteristics thereof, a motion caused by a biological body motion is generated in a screen in some cases.

The technology described in Patent Literature described above suppresses blurring on the basis of the manipulation situation information, but does not consider a motion caused by a biological body motion. Thus, if the technology tries to suppress blurring in accordance with a manipulation situation, a motion caused by a biological body motion is removed. This leads to such a problem that it becomes impossible to accurately observe a biological body motion.

In view of the foregoing, it has been demanded to correct blurring without removing a screen motion caused by a biological body motion.

Solution to Problem

According to the present disclosure, there is provided an image processing apparatus including: a blurring amount estimation unit configured to estimate a blurring amount of a medical image including a biological body motion of a subject; and a blurring correction processing unit configured to perform blurring correction processing so as not to remove a screen motion caused by the biological body motion, on a basis of the blurring amount.

In addition, according to the present disclosure, there is provided an image processing method including: estimating a blurring amount of a medical image including a biological body motion of a subject; and performing blurring correction processing so as not to remove a screen motion caused by the biological body motion, on a basis of the blurring amount.

In addition, according to the present disclosure, there is provided a medical system including: an imaging apparatus configured to capture a medical image including a biological body motion of a subject; and an image processing apparatus including a blurring amount estimation unit configured to estimate a blurring amount of the medical image, and a blurring correction processing unit configured to perform blurring correction processing so as not to remove a screen motion caused by the biological body motion, on a basis of the blurring amount.

Advantageous Effects of Invention

According to the present disclosure, it becomes possible to correct blurring without removing a screen motion caused by a biological body motion.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is a schematic diagram illustrating smoothing filters suitable for operative method modes, and frequency properties.

FIG. 4B is a schematic diagram illustrating an example of performing extraction of a color distribution and a spatial frequency distribution from an input image, automatically determining a clinical department or a scene of an operative method, and selecting a smoothing filter suitable for the scene.

FIG. 5 is a schematic diagram illustrating a configuration of a frequency analysis unit in detail.

FIG. 19 is a schematic diagram illustrating a configuration example of a case of obtaining a noise reduction effect on a moving image, by performing smoothing in a time direction filter according to the present embodiment.

MODE(S) FOR CARRYING OUT THE INVENTION

Figure 1:
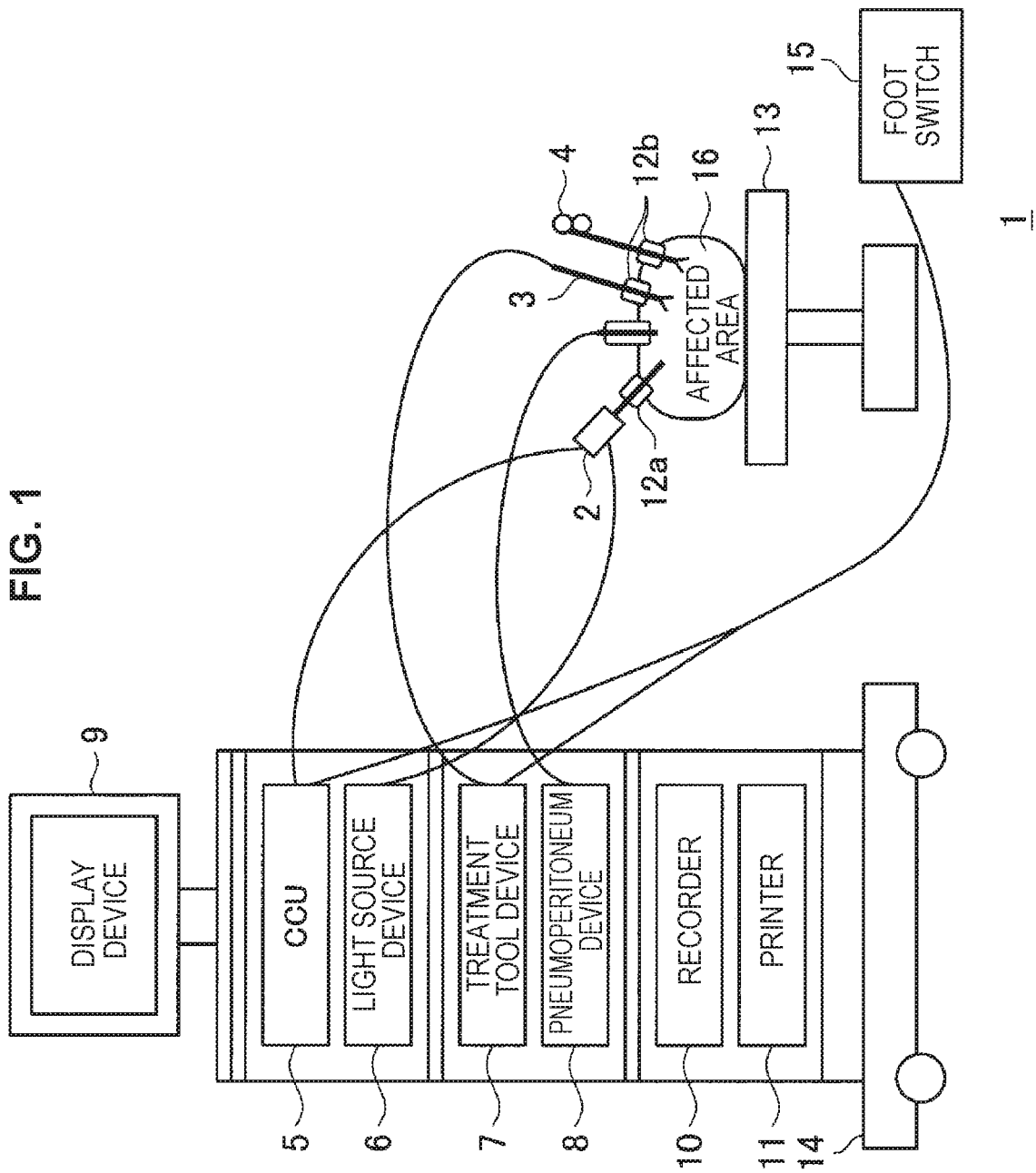
FIG. 1 is a schematic diagram illustrating a configuration of an endoscopic operation system.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that, the description will be given in the following order.

1. Configuration Example of Endoscopic Operation System
2. Configuration Example of Image Processing Apparatus
3. Example of Determining Operative Method from Input Image
4. Separation of Blurring That Is Based on Frequency Analysis
5. Decision of Correction Gain Suitable for Subject Position
6. Application to Microscopic Device 1. Configuration Example of Endoscopic Operation System In recent years, in the field site of medical treatment, endoscopic operation is performed in place of conventional open abdominal operation. For example, in the case of performing operation of an abdominal part, an endoscopic operation system 1 disposed in an operating room as illustrated in FIG. 1 is used. Instead of opening an abdominal part by cutting an abdominal wall as in the conventional operation, hole-opening tools referred to as trocars 12a and 12b are attached to several locations on an abdominal wall, and an abdominoscope (hereinafter, also referred to as an endoscope) 2, an energy treatment tool 3, forceps 4, and the like are inserted into a body from holes provided in the trocars 12a and 12b. Then, while viewing in real time an image of an affected area (tumor, etc.) 16 that has been captured as a video by the endoscope 2, treatment of cutting off the affected area 16 by the energy treatment tool 3 or the like, and the like are performed. The endoscope 2, the energy treatment tool 3, and the forceps 4 are held by an operator, an assistant, a scopist, a robot, or the like.

In an operating room in which such endoscopic operation is performed, a cart 14 on which devices for endoscopic operation are mounted, a patient bed 13 on which a patient lies, a foot switch 15, and the like are disposed. On the cart 14, for example, devices such as a camera control unit (CCU) 5, a light source device 6, a treatment tool device 7, a pneumoperitoneum device 8, a display device 9, a recorder 10, and a printer 11 are placed as medical devices.

An image signal of the affected area 16 imaged by an image sensor through an observation optical system of the endoscope 2 is transmitted to the CCU 5 via a camera cable, subject to signal processing in the CCU 5, and then, output to the display device 9, on which an endoscopic image of the affected area 16 is displayed. The CCU 5 may be wirelessly connected to the endoscope 2 in addition to being connected to the endoscope 2 via the camera cable.

The light source device 6 is connected to the endoscope 2 via a light guide cable, and can emit, to the affected area 16, light with various wavelengths while performing switching.

The treatment tool device 7 is a high frequency output device that outputs high frequency current to the energy treatment tool 3 that cuts off the affected area 16 using electrical heat, for example.

The pneumoperitoneum device 8 includes an air supply means and an air suction means, and supplies air into an abdominal region inside the body of the patient, for example.

The foot switch 15 controls the CCU 5, the treatment tool device 7, and the like using a foot manipulation performed by an operator, an assistant, or the like, as a trigger signal.

2. Configuration Example of Image Processing Apparatus

Figure 2:
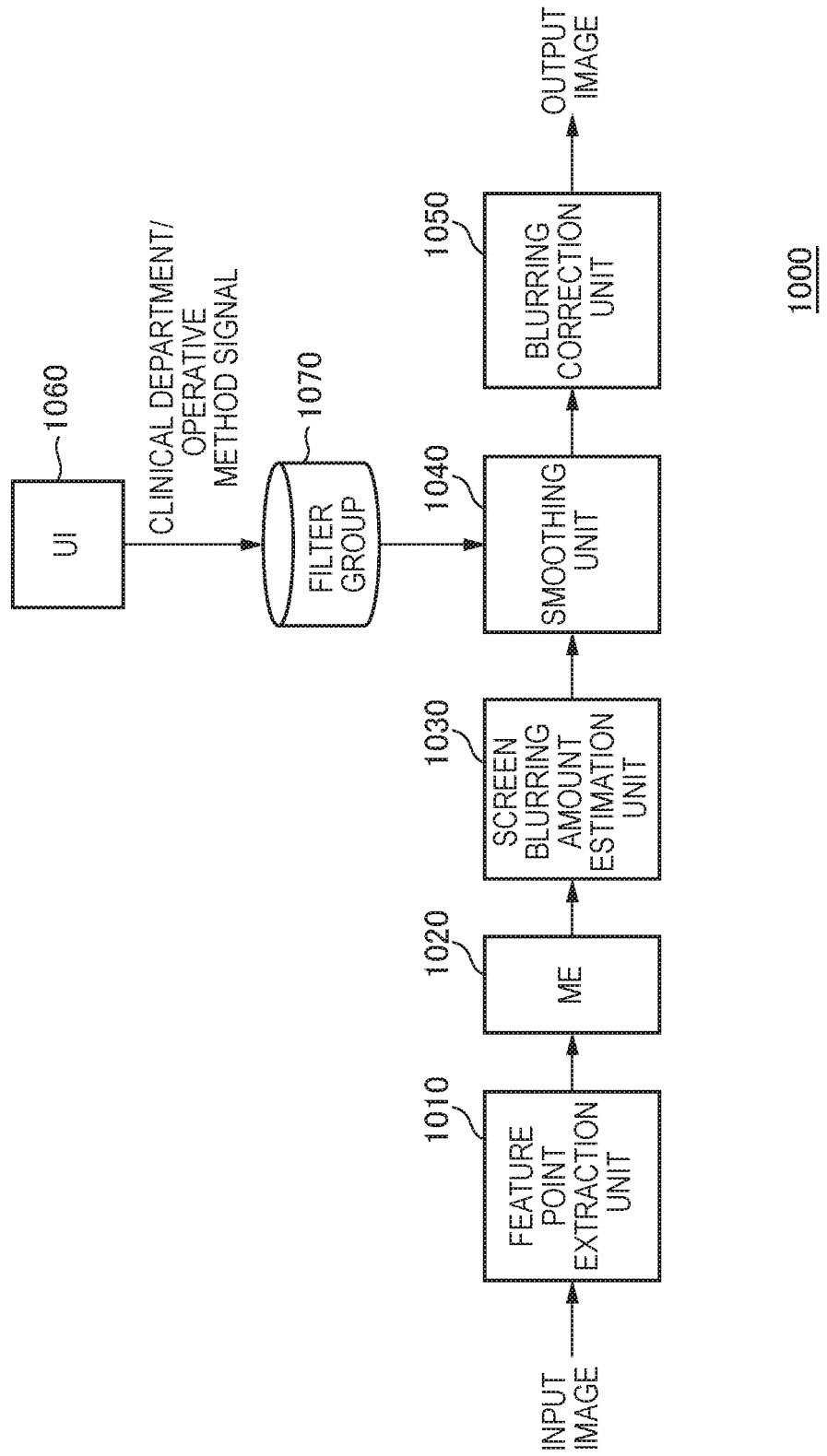
FIG. 2 is a schematic diagram illustrating a basic configuration of an image processing apparatus.

The present embodiment relates to a blurring correction technology for an endoscope, and relates to a technology of obtaining good image quality by appropriately suppressing a frequency component of blurring in accordance with an operative method of each clinical department that uses an endoscope. FIG. 2 is a schematic diagram illustrating a configuration of an image processing apparatus 1000 included in the CCU 5, and illustrates a basic configuration for blurring correction. As illustrated in FIG. 2, the image processing apparatus 1000 includes a feature point extraction unit 1010, a motion vector extraction unit (ME: Motion Estimation) 1020, an image burring amount estimation unit 1030, a smoothing unit 1040, a blurring correction unit 1050, a user interface (UI) 1060, and a filter group 1070. The filter group 1070 is stored in a database.

An input image imaged by an image sensor of the endoscope 2 is input to the feature point extraction unit 1010. The image sensor includes a complementary metal-oxide semiconductor (CMOS) sensor or the like, for example. The feature point extraction unit 1010 performs feature point extraction from each pixel of the input image. The motion vector extraction unit 1020 performs motion vector detection for the feature points. The image burring amount estimation unit 1030 estimates a blurring amount of the entire screen from a motion vector detection result of each feature point that has been obtained by the motion vector extraction unit 1020. The smoothing unit 1040 accumulates blurring amounts in a time direction, and performs smoothing by applying a filter to the accumulated blurring amounts. The blurring correction unit 1050 performs blurring correction on the smoothed blurring amounts.

The estimation of the blurring amount that is performed by the image burring amount estimation unit 1030 can be performed by a method such as Random Sample Consensus (RANSAC), for example. In this case, samples of motion vectors are extracted at random, and samples with little errors among all the samples are counted. Then, by employing a coefficient having the largest number of samples with little errors, and the samples, a least-square method is performed using only effective components in a state in which error components are excluded, and a coefficient is estimated. The blurring amount of the entire screen can be thereby estimated from a motion vector of each feature point.

When blurring amounts in the time direction are accumulated by the smoothing unit 1040, blurring frequencies are obtained. By applying a smoothing filter to the blurring frequencies, a smoothing unit 104 leaves only a desired frequency component, and removes unnecessary frequency components. For example, a bandpass filter (BPF) is used as the smoothing filter. This can leave, as a blurring correction target, only a frequency for which blurring is desired to be suppressed, and can avoid setting a frequency for which blurring is undesired to be suppressed, as a blurring correction target.

On the basis of the smoothed blurring amounts, the blurring correction unit 1050 performs blurring correction on the input image by a publicly-known method such as affine transformation, for example. Note that, a blurring correction processing unit according to the present embodiment includes the smoothing unit 1040 and the blurring correction unit 1050.

In the configuration example illustrated in FIG. 2, a user selects an operative method mode in accordance with an operation scene, via the user interface (UI) 1060. FIG. 3 is a schematic diagram illustrating smoothing filters suitable for operative method modes, and frequency properties of the smoothing filters. In accordance with an operative method mode selected by the user, a smoothing filter having a frequency property of optimally suppressing blurring is selected from among the filter group 1070, in accordance with an operative method of each clinical department (oto-rhinolaryngology, digestive surgery, orthopedic surgery) as illustrated in FIG. 3. The smoothing unit 1040 performs smoothing by the selected smoothing filter.

The smoothing filters illustrated in FIG. 3 include a low pass filter (LPF), for example. In the case of the otorhino-laryngology, by the low pass filter, blurring with a frequency of 3 to 5 [Hz] or more is suppressed, and blurring with a frequency of less than 3 to 5 [Hz] is left. In the case of the digestive surgery, by the low pass filter, blurring with a frequency of 8 to 10 [Hz] or more is suppressed, and blurring with a frequency of less than 8 to 10 [Hz] is left. In the case of the orthopedic surgery, blurring with a frequency of 4 to 6 [Hz] or more is suppressed, and blurring with a frequency of less than 4 to 6 [Hz] is left.

Because devices such as the endoscope 2 that are used in operation vary depending on a difference in clinical department, correction target blurring included in a capture image varies for each clinical department. In the present embodiment, because it becomes possible to suppress blurring in accordance with an operative method of each clinical department, an optimum image with corrected blurring can be obtained for each clinical department.

3. Example of Determining Operative Method from Input Image

Figure 4A:
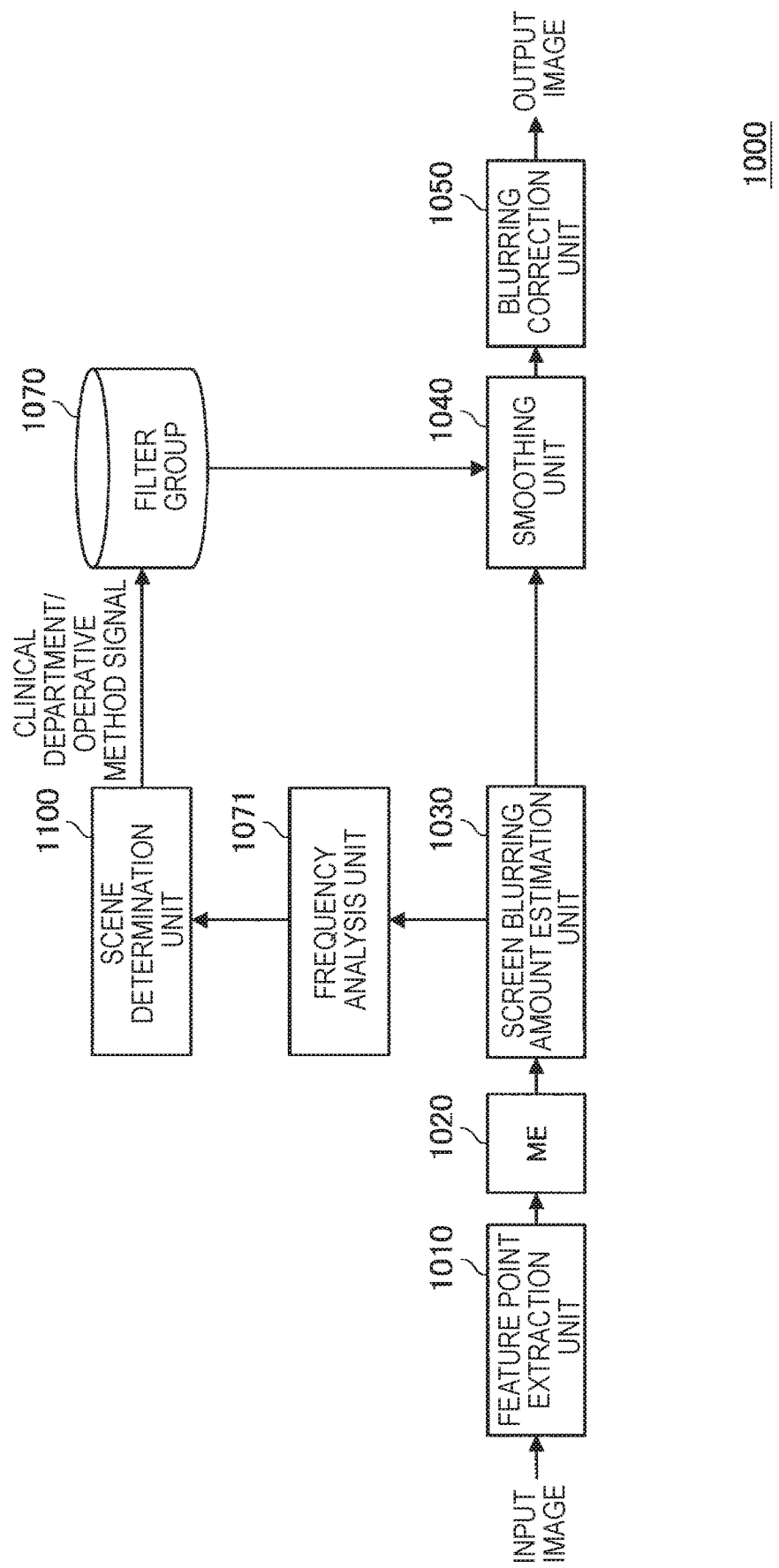
FIG. 4A is a schematic diagram illustrating an example of performing frequency analysis from a screen blurring amount of an input image, automatically determining a clinical department or a scene of an operative method, and selecting a smoothing filter suitable for the scene.

In FIG. 2, it is assumed that the user selects an operative method mode. Alternatively, an operative method can also be determined from an input image. FIG. 4A illustrates an example of performing frequency analysis from a screen blurring amount of an input image, automatically determining a clinical department or a scene of an operative method that corresponds to the input image, from a result of the frequency analysis, and selecting a smoothing filter suitable for the scene, from the filter group 1070. Thus, in the example illustrated in FIG. 4A, a frequency analysis unit 1071 and a scene determination unit 1100 are further included in addition to the configuration in FIG. 2.

FIG. 5 is a schematic diagram illustrating a configuration of the frequency analysis unit 1071 in detail. As illustrated in FIG. 5, the frequency analysis unit 1071 includes a buffer 1072, a fast Fourier transformation unit (FFT) 1074, a frequency component extraction unit 1076, a normalization unit 1078, a filter selection signal generation unit 1080, an integration unit 1082, gain adjustment units 1084, 1086, and 1088, and a multiplication unit 1090.

As a screen blurring amount of an input image, a shift amount of the image is input to the frequency analysis unit 1071 from a screen blurring amount estimation unit 1030. The shift amount is accumulated into the buffer 1072, and then, frequency transformation is performed by the fast Fourier transformation unit (FFT) 1074. By extracting frequency components by the frequency component extraction unit 1076, it is determined which frequency is largely included, and normalization is performed by the normalization unit 1078. Then, on the basis of a result of the normalization, a filter selection signal for selecting a filter is generated by the filter selection signal generation unit 1080, and the filter selection signal is output.

In addition, the frequency analysis unit 1071 performs gain adjustment by the gain adjustment units 1084, 1086, and 1088 using adjustment values A, B, C, D, and E. The integration unit 1082 integrates shift amounts with a frame number N2 that are accumulated in the buffer 1072, and the gain adjustment unit 1084 reduces a gain as a value of integral becomes larger, on the basis of the integrated shift amounts.

In addition, on the basis of the shift amount, the gain adjustment unit 1086 reduces a gain as the shift amount becomes larger. In addition, in accordance with reliability of a blurring amount (motion reliability as to whether a unit matrix has been obtained, etc.) that has been estimated by the screen blurring amount estimation unit 1030, the gain adjustment unit 1088 adjusts a gain so as to reduce the gain as the reliability becomes lower. Particularly in a case where the reliability is a certain value or less, the gain adjustment unit 1088 sets the gain to 0, and avoids performing blurring correction.

The gains calculated by the gain adjustment units 1084, 1086, and 1088 are multiplied by the multiplication unit 1090, and are output to the blurring correction unit 1050. The blurring correction unit 1050 adjusts the strength of blurring correction on the basis of the gains. By performing exceptional processing by the gain adjustment units 1084, 1086, and 1088, blurring correction can be inhibited from being excessively performed.

The filter selection signal output by the frequency analysis unit 1071 is input to the scene determination unit 1100. The scene determination unit 1100 determines a scene of an operative method on the basis of the filter selection signal, and selects an optimum smoothing filter suitable for the scene of the operative method, from among the filter group 1070. The smoothing unit 1040 performs smoothing by the selected smoothing filter.

FIG. 4B illustrates an example of performing extraction of a color distribution and a spatial frequency distribution from an input image, automatically determining a clinical department or a scene of an operative method that corresponds to the input image, from these pieces of information, and selecting a smoothing filter suitable for the scene, from the filter group 1070. Thus, in the example illustrated in FIG. 4B, a color distribution extraction unit 1110, a spatial frequency distribution extraction unit 1112, and the scene determination unit 1100 are further included in addition to the configuration in FIG. 2. The color distribution extraction unit 1110 extracts a color distribution of the input image. The spatial frequency distribution extraction unit 1112 extracts a spatial frequency distribution of the input image. On the basis of the color distribution and the spatial frequency distribution of the input image, the scene determination unit 1100 determines a clinical department or a scene of an operative method that corresponds to the input image, and selects an optimum smoothing filter suitable for the scene of the operative method, from among the filter group 1070. The smoothing unit 1040 performs smoothing by the selected smoothing filter.

Figure 4C:
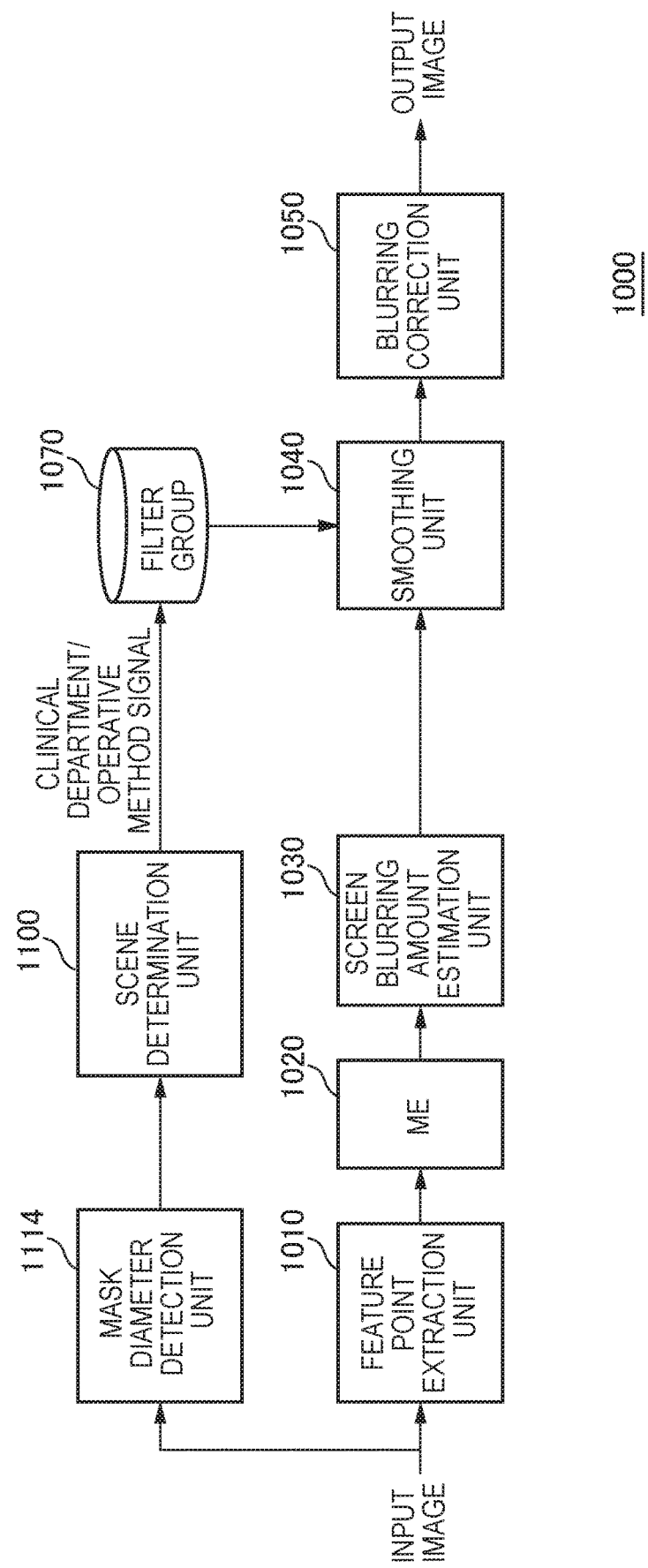
FIG. 4C is a schematic diagram illustrating an example of performing detection of a mask diameter from an input image, automatically determining a clinical department or a scene of an operative method, and selecting a smoothing filter suitable for the scene.

FIG. 4C illustrates an example of performing detection of a mask diameter from an input image, automatically determining a clinical department or a scene of an operative method that corresponds to the input image, from information regarding the mask diameter, and selecting a smoothing filter suitable for the scene, from the filter group 1070. Thus, in the example illustrated in FIG. 4C, a mask diameter extraction unit 1114 and the scene determination unit 1100 are further included in addition to the configuration in FIG. 2. A mask diameter extraction unit 114 detects a mask diameter from the input image. On the basis of the mask diameter, the scene determination unit 1100 determines a clinical department or a scene of an operative method that corresponds to the input image, and selects an optimum smoothing filter suitable for the scene of the operative method, from among the filter group 1070. The smoothing unit 1040 performs smoothing by the selected smoothing filter. On the basis of the mask diameter, the feature point extraction unit 1010 can extract a feature point from a narrower range in a mask, as the mask diameter becomes smaller.

Figure 4D:
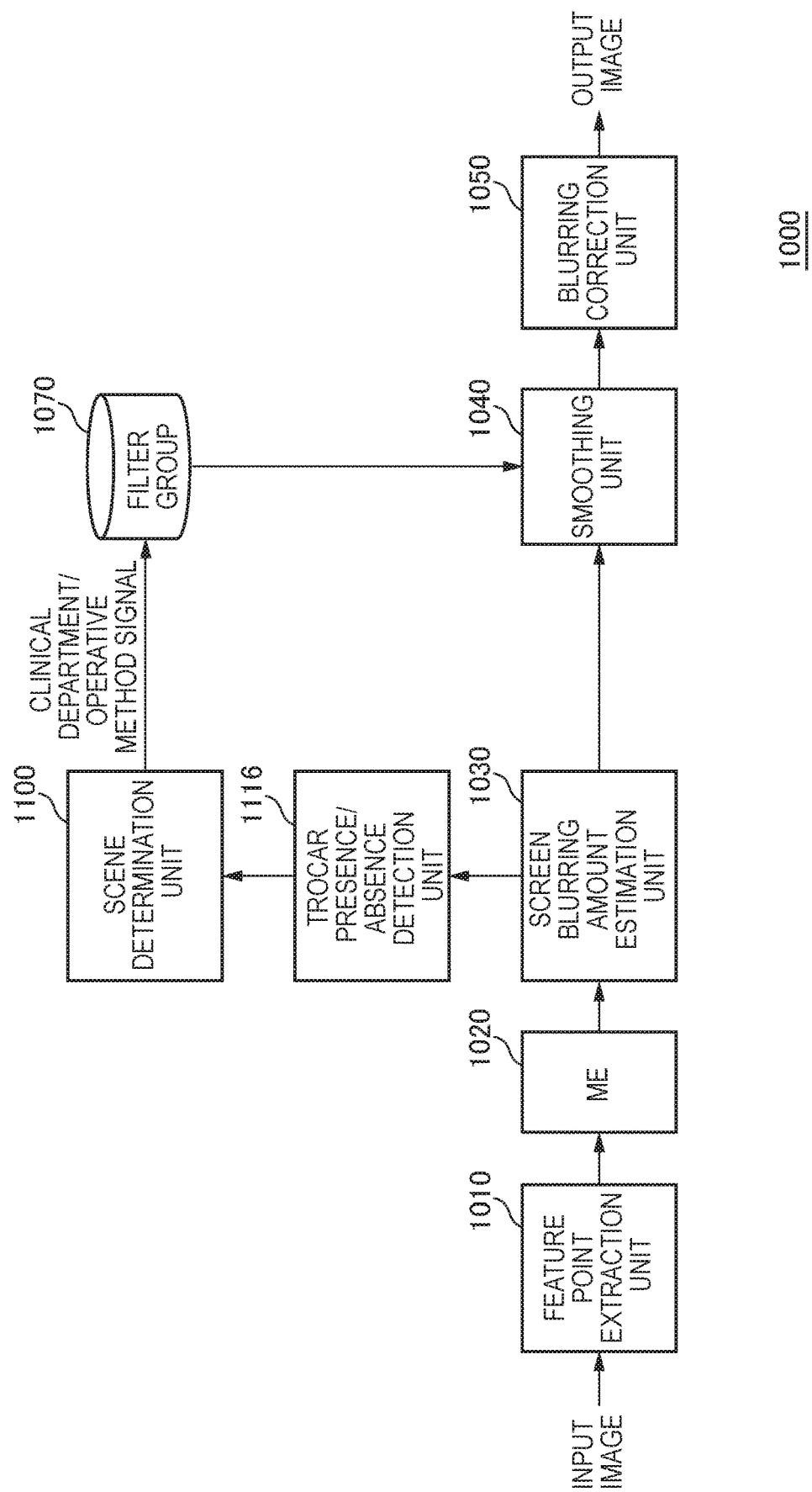
FIG. 4D is a schematic diagram illustrating an example of detecting the presence or absence of trocars from an input image, automatically determining a clinical department or a scene of an operative method, and selecting a smoothing filter suitable for the scene.

FIG. 4D illustrates an example of detecting the presence or absence of trocars from an input image, automatically determining a clinical department or a scene of an operative method that corresponds to the input image, from these pieces of information, and selecting a smoothing filter suitable for the scene, from the filter group 1070. Thus, in the example illustrated in FIG. 4D, a trocar presence/absence detection unit 1116 and the scene determination unit 1100 are further included in addition to the configuration in FIG. 2. On the basis of a screen blurring amount estimated by the screen blurring amount estimation unit 1030, the trocar presence/absence detection unit 1116 detects whether or not the trocars 12a and 12b are used (the presence or absence of the trocars). On the basis of the presence or absence of the trocars 12a and 12b, the scene determination unit 1100 determines a clinical department or a scene of an operative method that corresponds to the input image, and selects an optimum smoothing filter suitable for the scene of the operative method, from among the filter group 1070. The smoothing unit 1040 performs smoothing by the selected smoothing filter.

A determination method of a clinical department or an operative method can be performed in accordance with information such as a motion frequency analysis result of a moving image, operative method/scene recognition, information regarding a mask diameter, and the presence or absence of the trocars 12a and 12b, as illustrated in Table 1. As for the frequency analysis of a motion, in accordance with a peak position of a frequency component, a clinical department can be decided to be orthopedic surgery if the peak position is 3 to 5 [Hz], to be an otorhinolaryngology if the peak position is 4 to 6 [Hz], or to be digestive surgery if the peak position is 8 to 10 [Hz]. According to the configuration example illustrated in FIG. 4A, in accordance with a result of frequency analysis, a clinical department or a scene of an operative method can be determined on the basis of Table 1.

As for operative method/scene recognition performed by the extraction of a color distribution and a spatial frequency distribution that is illustrated in FIG. 4B, a clinical department is determined to be otorhinolaryngology in a case where red regions are largely included in the input image, the image is flat, and a spatial frequency is low, or to be orthopedic surgery in a case where white regions are largely included, the image is flat, and a spatial frequency is low, as illustrated in Table 1. Alternatively, in a case where various color components are largely included in the input image, there are textures in blood vessels and fat, and a spatial frequency is high, a clinical department is determined to be digestive surgery.

In the determination that is based on information regarding a mask diameter that is illustrated in FIG. 4C, the mask diameter extraction unit 1114 detects a mask diameter from the input image, and a clinical department is determined to be otorhinolaryngology if the mask diameter is about 4.9 mm, to be orthopedic surgery if the mask diameter is about 5.5 mm, or to be digestive surgery if the mask diameter is about 10 mm, as illustrated in Table 1. In this manner, because a mask diameter varies depending on the clinical department or the scene of the operative method, by detecting a mask diameter, a clinical department or a scene of an operative method can be determined.

In addition, in a case where the trocars 12a and 12b are used, because the trocars 12a and 12b serve as fulcrum points, many of the motions of the endoscope 2 become presupposed decided motions. Thus, a frequency of a screen blurring amount varies between a case where the trocars 12a and 12b are used, and a case where the trocars 12a and 12b are not used. Thus, a trocar presence/absence detection unit 116 in FIG. 4D can determine whether or not the trocars 12a and 12b are used, on the basis of a frequency of a screen blurring amount. As illustrated in Table 1, in a case where the trocars 12a and 12b are used, a clinical department can be determined to be digestive surgery, and in a case where the trocars 12a and 12b are not used, a clinical department can be determined to be orthopedic surgery or otorhinolaryngology.

TABLE 1

|  | Motion frequency [Hz] | Operative method/scene recognition | Mask diameter [mm] | Presence or absence of trocars |
|---|---|---|---|---|
| Otorhinolaryngology Nasotracheal operation | 3-5 or more | Many red regions, flat, low spatial frequency | 4.9 | Absent |
| Orthopedic surgery Knee joint operation | 4-6 or more | Many white regions, flat, low spatial frequency | 5.5 | Absent |
| Digestive surgery | 8-10 or more | Various color components are included, there are textures in blood vessels and fat, high spatial frequency | 10 | Present |

Table 2 shown below indicates "blurring" desired to be suppressed, and a frequency thereof, and "blurring" undesired to be suppressed, and a frequency thereof, in each clinical department. Using a determination result, an optimum smoothing filter is applied to each of the "blurring" desired to be suppressed and the "blurring" undesired to be suppressed. In any clinical department, a smoothing filter is selected so as not to remove a screen motion caused by a biological body motion, by blurring correction. By selecting a smoothing filter in accordance with each clinical department or operative method on the basis of Table 2, blurring caused by factors such as the shake of an endoscopic scope and the vibration of a building or an arm is set as a target of blurring correction to be performed by the blurring correction unit 1050, and a motion intended by an operator or a motion of a biological main body is prevented from being set as a target of blurring correction to be performed by the blurring correction unit 1050. Note that, when these pieces of operative method information are transmitted to the CCU 5, not only a cable but also a Radio Frequency Identification (RFID) or the like can also be used.

4. Separation of Blurring That Is Based on Frequency Analysis

Figure 6A:
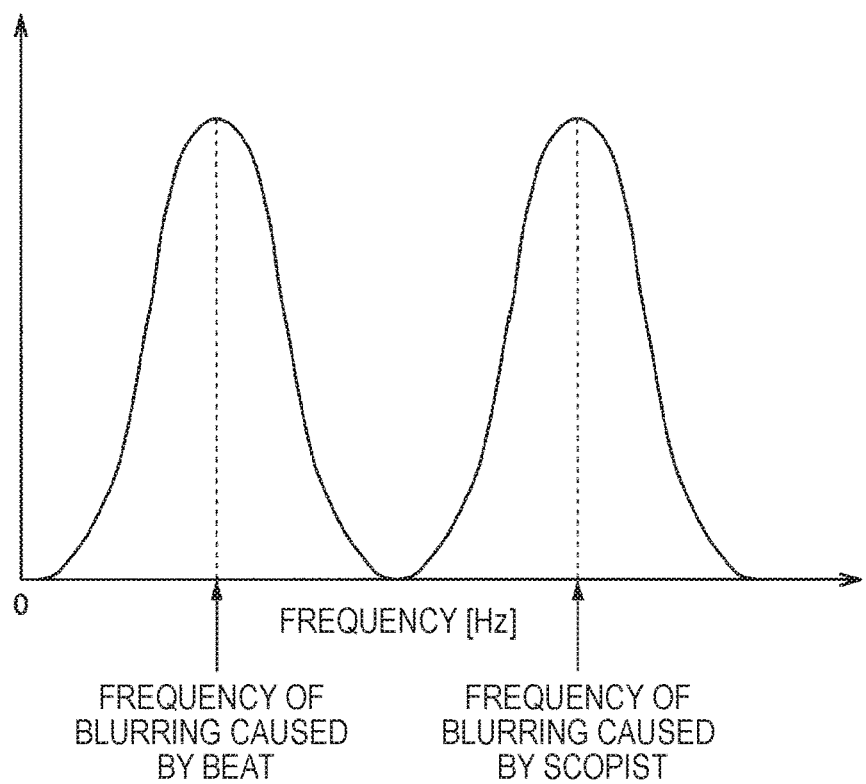
FIG. 6A is a property diagram illustrating frequencies of blurring caused by a beat, and blurring caused by a scopist.
Figure 6B:
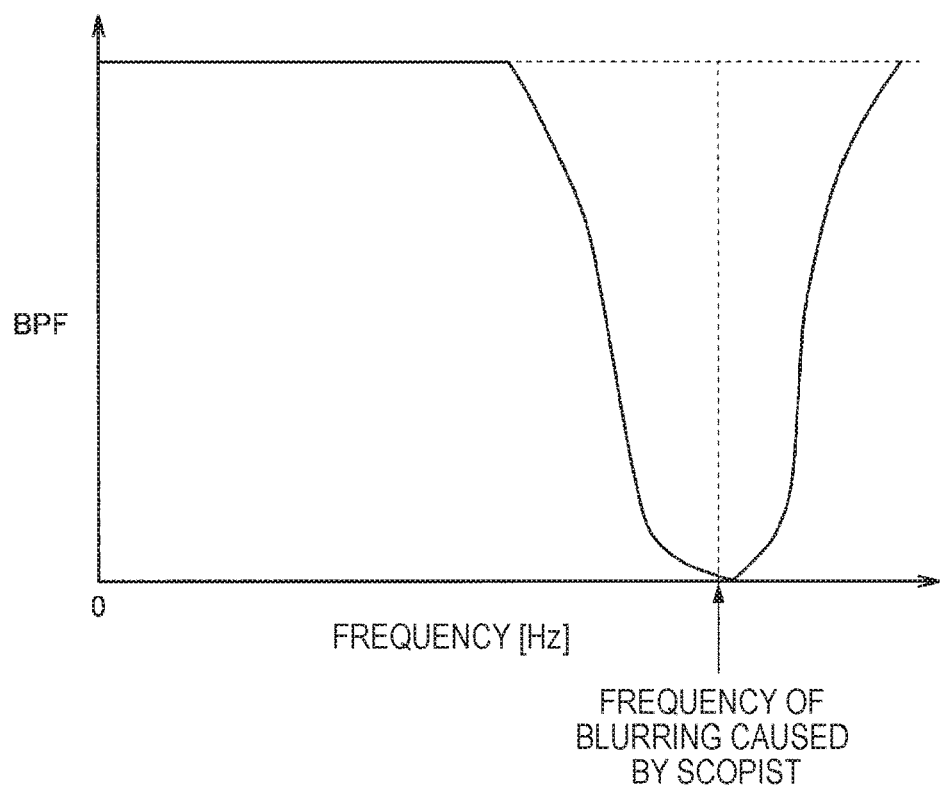
FIG. 6B is a property diagram illustrating a property of a bandpass filter (BPF) for suppressing blurring caused by a scopist.

In the configuration examples illustrated in FIGS. 4A, 4B, 4C, and 4D, blurring caused by an operator or a scopist, and blurring caused by a patient (beat, etc.) can be separated from each other on the basis of frequency analysis. FIG. 6A is a property diagram illustrating frequencies of blurring caused by a beat, and blurring caused by a scopist. In addition, FIG. 6B is a property diagram illustrating a property of a bandpass filter (BPF) for suppressing blurring caused by a scopist. In this manner, an arbitrary blurring frequency can also be suppressed using the bandpass filter (BPF) instead of a low pass filter (LPF) as illustrated in FIG. 3. In this case, a bandpass filter is stored in the filter group 1070, and a bandpass filter is selected on the basis of frequency analysis. As the configuration, a configuration similar to those of FIGS. 4A, 4B, 4C, and 4D can be employed.

5. Decision of Correction Gain Suitable for Subject Position

Figure 7:
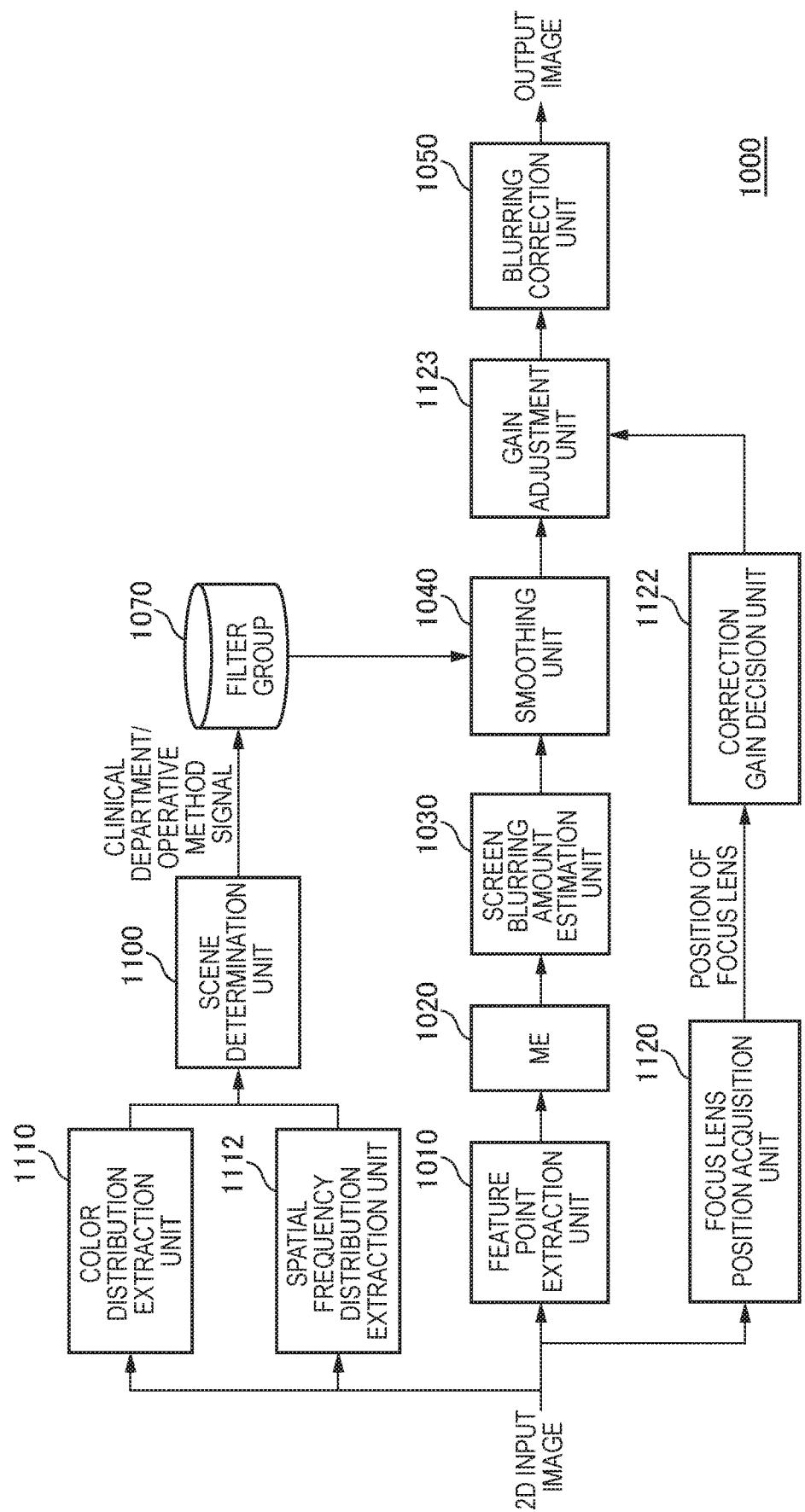
FIG. 7 is a schematic diagram illustrating a configuration of acquiring focus lens position information of an endoscopic scope, and deciding a correction gain.

FIG. 7 is a schematic diagram illustrating a configuration of acquiring focus lens position information of the endoscope 2, and deciding a correction gain. In addition to the configurations in FIGS. 4A and 4B, gain adjustment for blurring correction is performed in accordance with a distance between the endoscope 2 and a subject. Thus, in the

TABLE 2

|  | Cause of blurring desired to be suppressed | Frequency [Hz] (*) | Cause of blurring undesired to be suppressed | Frequency [Hz] |
|---|---|---|---|---|
| Otorhinolaryngology | Scope shake | 3-5 or more | Scope motion intended by operator | Less than 3-5 |
| Orthopedic surgery | Scope shake | 4-6 or more | Scope motion intended by operator | Less than 4-6 |
| Digestive surgery | Scope shake, blurring generated when touching | 8-10 or more | Original motion of biological body, scope motion intended by operator | Less than 8-10 |
| Cranial nerve surgery (VM) | Blurring caused by vibration of building, shake of arm itself | 0-1, 8-9, or more | Original motion of biological body | (0 or 1)-(8 or 9) | configuration illustrated in FIG. 7, a focus lens position acquisition unit 1120, a correction gain decision unit 1122, and a gain adjustment unit 1123 are included in addition to the configuration in FIG. 4B.

Figure 8:
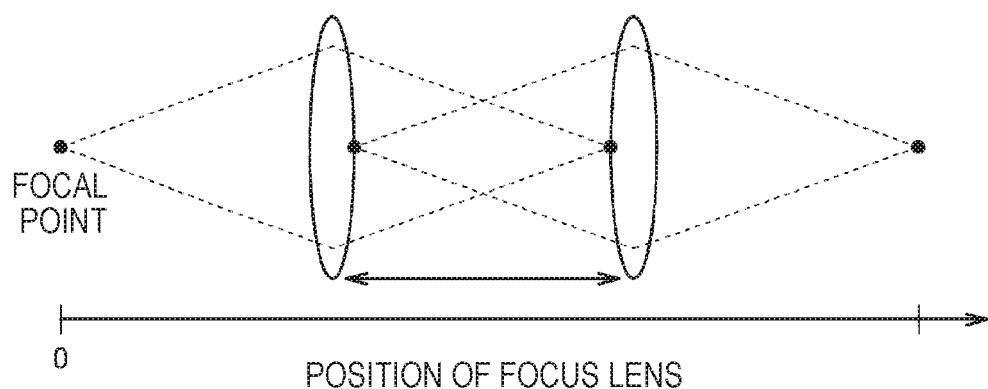
FIG. 8 is a schematic diagram illustrating a focus lens position.
Figure 9:
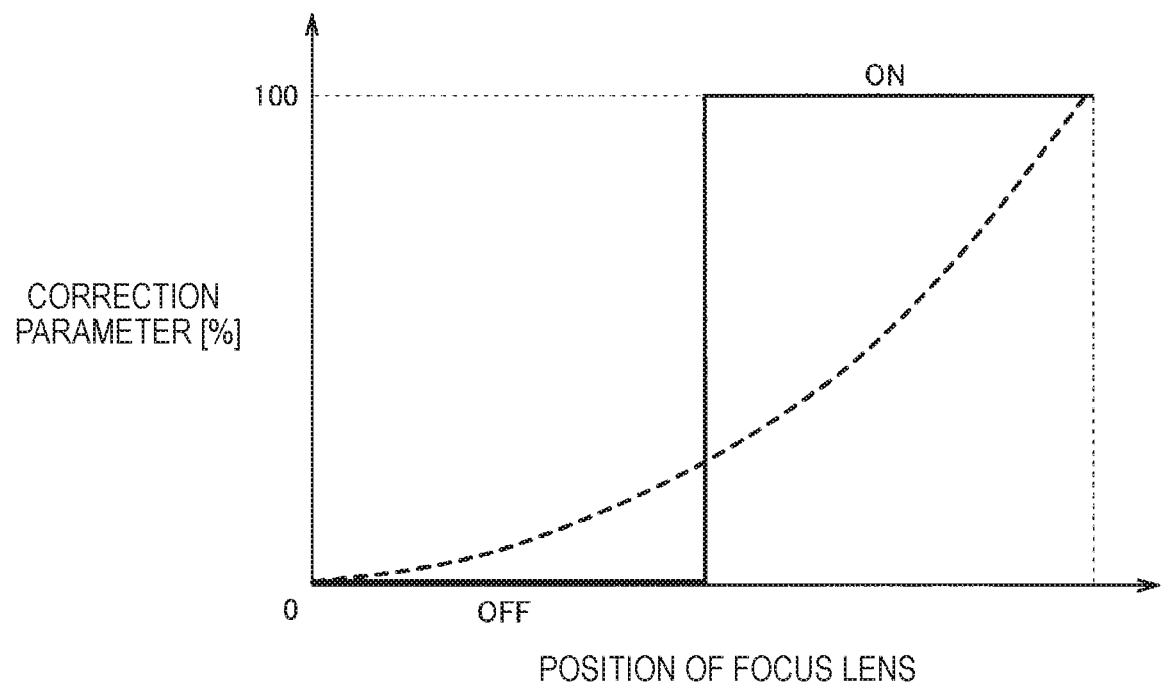
FIG. 9 is a schematic diagram illustrating a relationship between a distance between a subject and the endoscopic scope, and a correction gain (correction parameter).

In the configuration example illustrated in FIG. 7, focus lens position information of the endoscope 2 is acquired, and a correction gain is decided. FIG. 8 is a schematic diagram illustrating a focus lens position. Because a relationship between a distance to a subject and a focus lens position is unambiguously defined, by adjusting a gain on the basis of the focus lens position information, it becomes possible to perform gain adjustment suitable for a distance to the subject. FIG. 9 is a schematic diagram illustrating a relationship between a focus lens position and a correction gain (correction parameter). The focus lens position acquired by the focus lens position acquisition unit 1120 is transmitted to the correction gain decision unit 1122, and the correction gain decision unit 1122 decides a correction gain on the basis of the property in FIG. 9.

In FIG. 9, it is assumed that a distance to the subject becomes larger as the focus lens position becomes larger. Thus, as a distance to the subject becomes larger, a value of a correction gain becomes larger. Because the distortion of the image that is caused by the shake of the endoscope 2 becomes larger as a distance to the subject becomes larger, the strength of blurring correction is enhanced by increasing a value of a correction gain as a distance to the subject becomes larger. It thereby becomes possible to optimally correct blurring in accordance with a distance to the subject. Note that, gain adjustment may be consecutively performed as indicated by a broken line in FIG. 9, or on/off may be controlled by discretely changing a correction gain as indicated by a solid line in FIG. 9.

Figure 10:
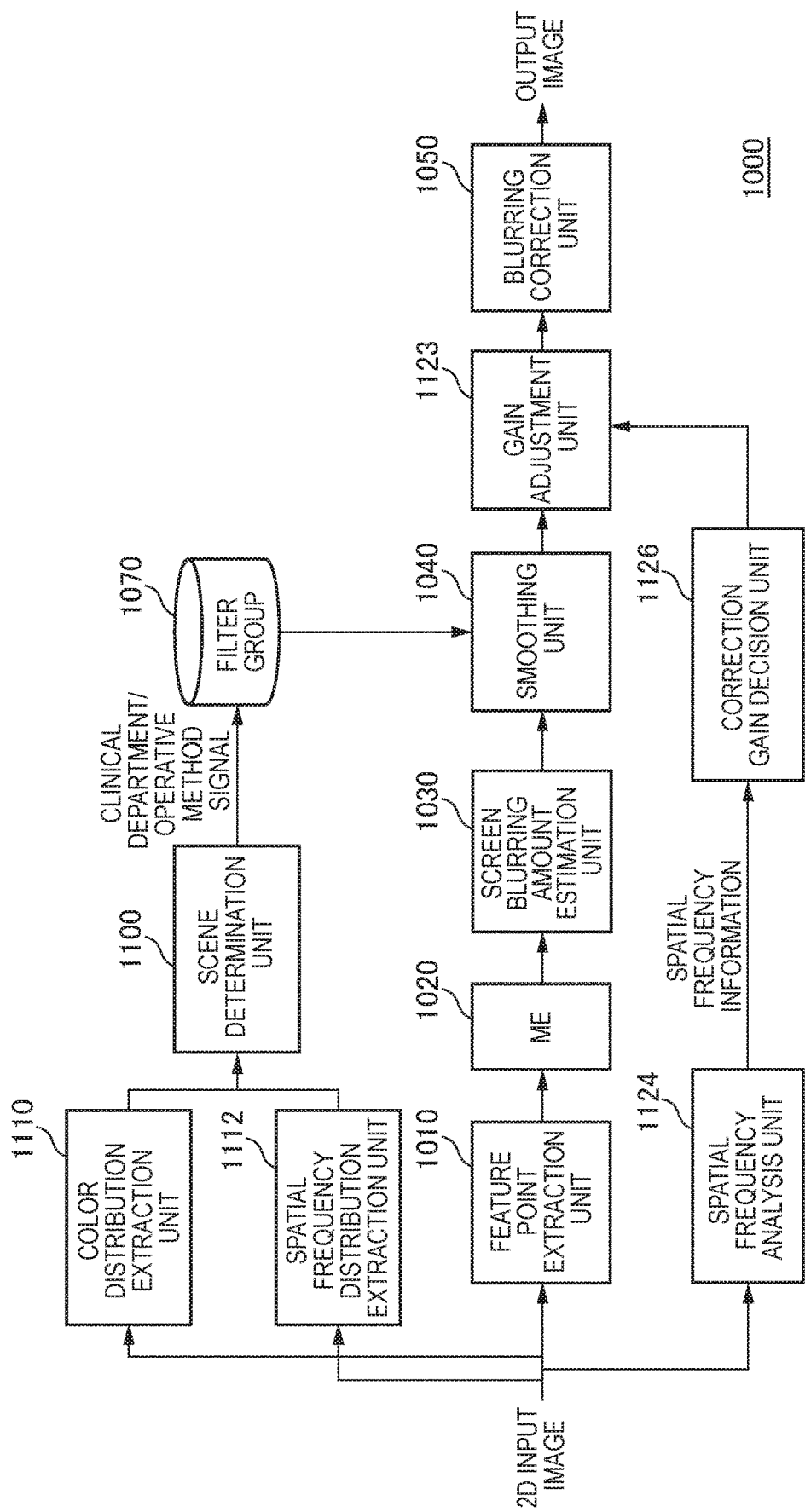
FIG. 10 is a schematic diagram illustrating a configuration example of acquiring a distance between the endoscopic scope and the subject on the basis of a spatial frequency of an image.
Figure 11:
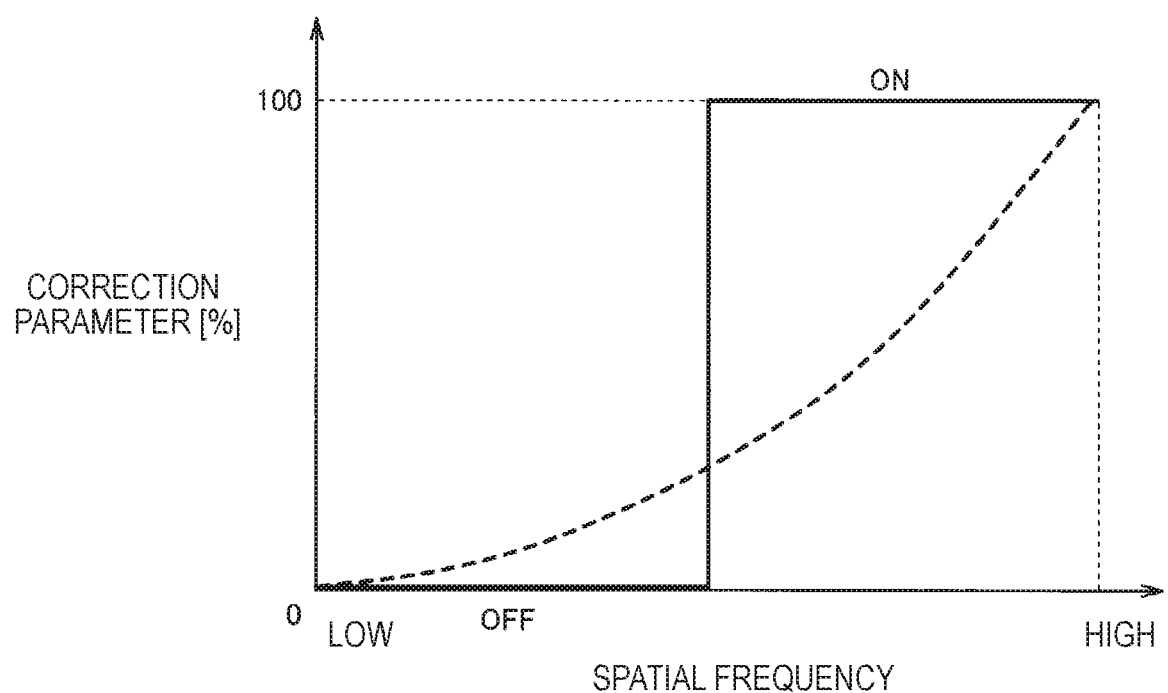
FIG. 11 is a schematic diagram illustrating a relationship between a spatial frequency and a correction gain (correction parameter).

FIG. 10 is a schematic diagram illustrating a configuration example of acquiring a distance between the endoscope 2 and the subject on the basis of a spatial frequency of an image. Thus, in the configuration illustrated in FIG. 10, a spatial frequency analysis unit 1124, a correction gain decision unit 1126, and the gain adjustment unit 1123 are included in addition to the configuration in FIG. 4B. The spatial frequency analysis unit 1124 analyzes a spatial frequency of the image. In a case where the endoscope 2 comes close to the subject, a spatial frequency of an image to be obtained becomes low, and in a case where the endoscope 2 goes away from the subject, the spatial frequency becomes higher. FIG. 11 is a schematic diagram illustrating a relationship between a spatial frequency and a correction gain (correction parameter). The spatial frequency analyzed by the spatial frequency analysis unit 1124 is transmitted to the correction gain decision unit 1126, and the correction gain decision unit 1126 decides a correction gain on the basis of the property in FIG. 11. Note that, gain adjustment may be consecutively performed as indicated by a broken line in FIG. 11, or on/off may be controlled by discretely changing a correction gain as indicated by a solid line in FIG. 11.

As illustrated in FIG. 11, as a spatial frequency becomes lower, that is to say, as the subject comes close, a correction gain becomes lower. In addition, as a spatial frequency becomes higher, that is to say, as the subject goes away, a correction gain becomes higher. As described above, because the distortion of the image that is caused by the shake of the endoscope 2 becomes larger as a distance to the subject becomes larger, the strength of blurring correction is enhanced by increasing a value of a correction gain as a distance to the subject becomes larger. It thereby becomes possible to optimally correct blurring in accordance with a distance to the subject.

Figure 12:
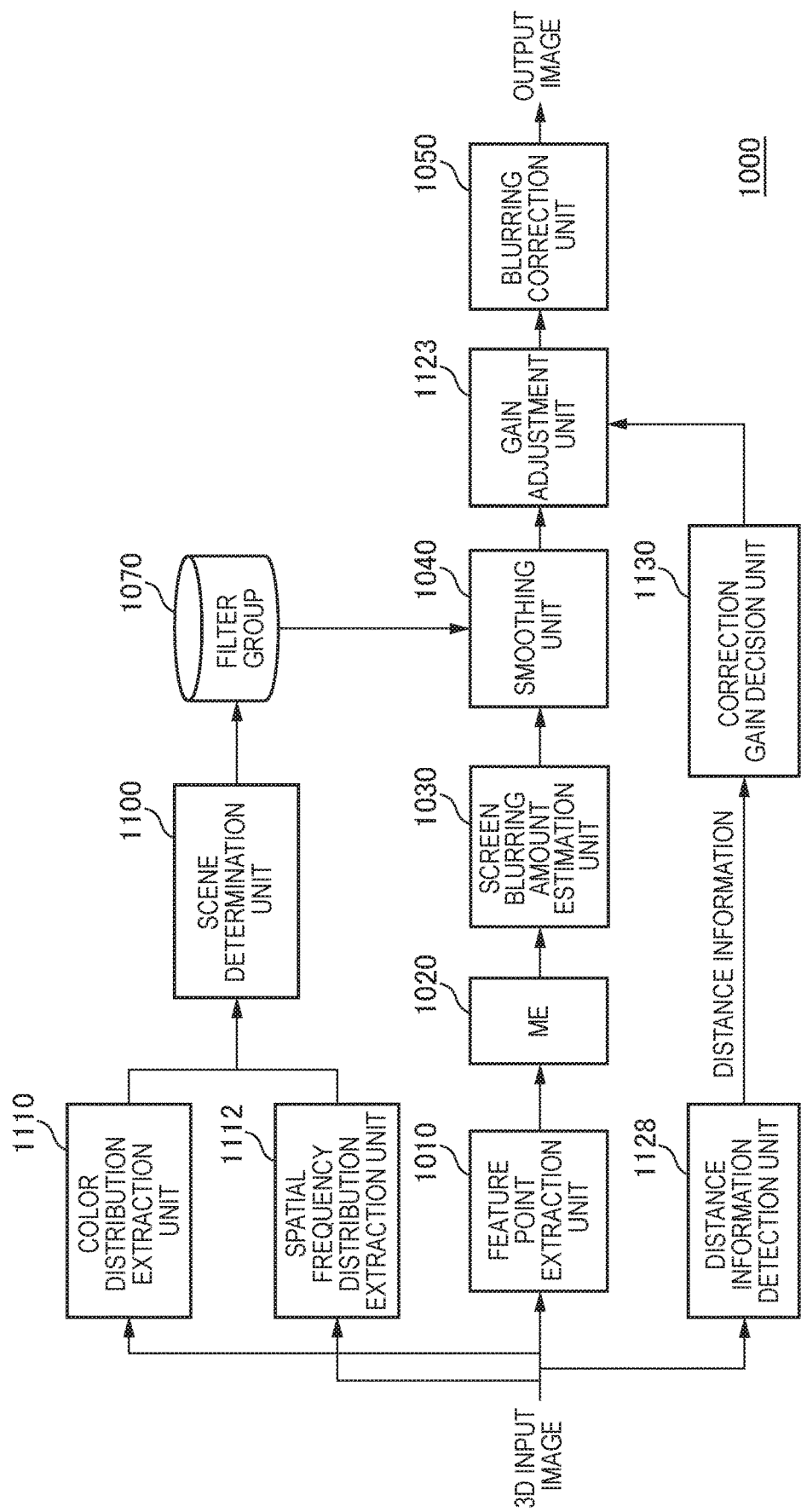
FIG. 12 is a schematic diagram illustrating a configuration example of acquiring a distance between the endoscopic scope and the subject in a stereo view, in a case where an endoscope performs two-lens stereo shooting.
Figure 13:
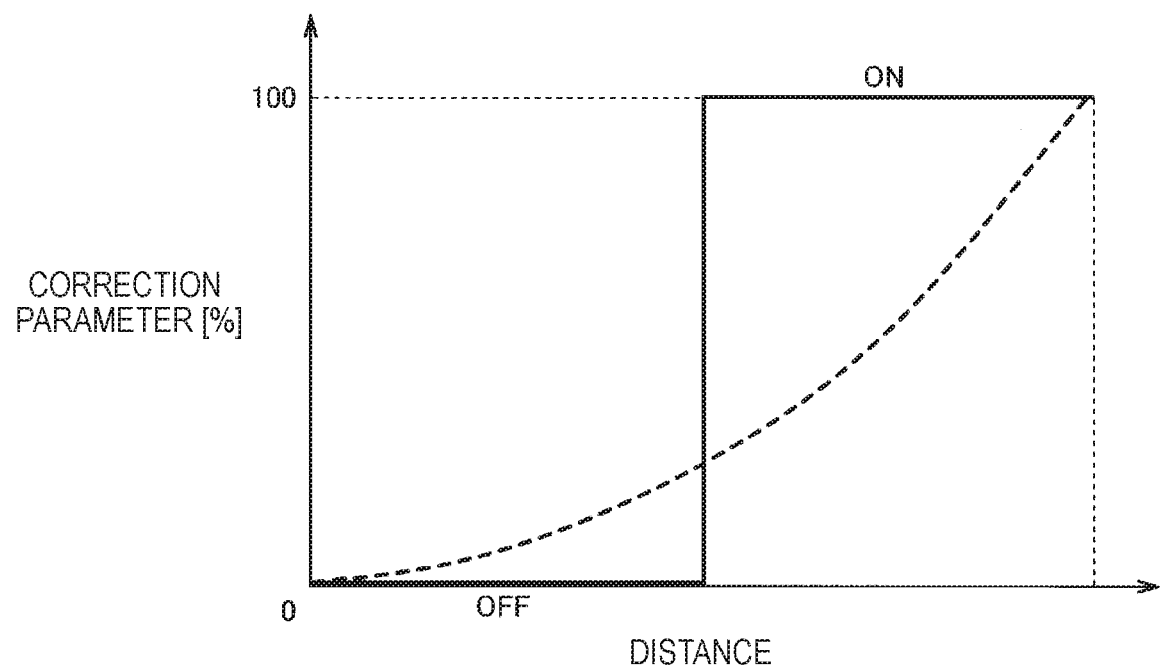
FIG. 13 is a schematic diagram illustrating a relationship between a distance to the subject, and a correction gain (correction parameter).

FIG. 12 is a schematic diagram illustrating a configuration example of acquiring a distance between the endoscope 2 and the subject in a stereo view, in a case where the endoscope 2 performs two-lens stereo shooting. Thus, in the configuration illustrated in FIG. 12, a distance information detection unit 1128, a correction gain decision unit 1130, and the gain adjustment unit 1123 are included in addition to the configuration in FIG. 4B. The distance information detection unit 1128 detects a distance to the subject on the basis of disparity of a stereo image. FIG. 13 is a schematic diagram illustrating a relationship between a distance to the subject, and a correction gain (correction parameter). A distance to the subject that has been detected by the distance information detection unit 1128 is transmitted to the correction gain decision unit 1130, and the correction gain decision unit 1130 decides a correction gain on the basis of the property in FIG. 13. Note that, gain adjustment may be consecutively performed as indicated by a broken line in FIG. 13, or on/off may be controlled by discretely changing a correction gain as indicated by a solid line in FIG. 13.

Also in FIG. 13, as the subject comes close, a correction gain becomes lower. In addition, as the subject goes away, a correction gain becomes higher. As described above, because the distortion of the image that is caused by the shale of the endoscope 2 becomes larger as a distance to the subject becomes larger, the strength of blurring correction is enhanced by increasing a value of a correction gain as a distance to the subject becomes larger. It thereby becomes possible to optimally correct blurring in accordance with a distance to the subject.

Figure 14:
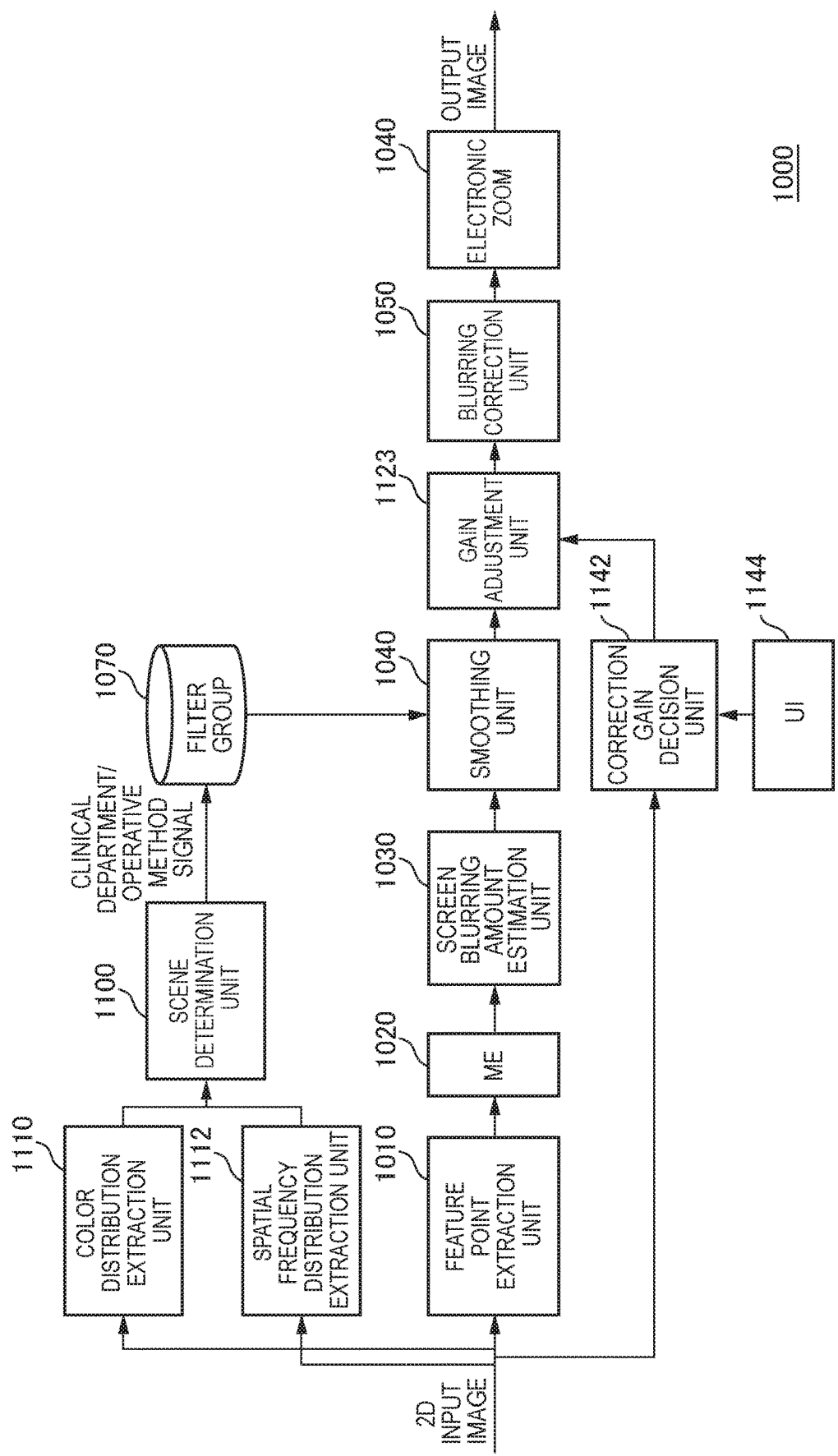
FIG. 14 is a schematic diagram illustrating a configuration example of a case of performing electronic zoom after blurring correction.
Figure 15:
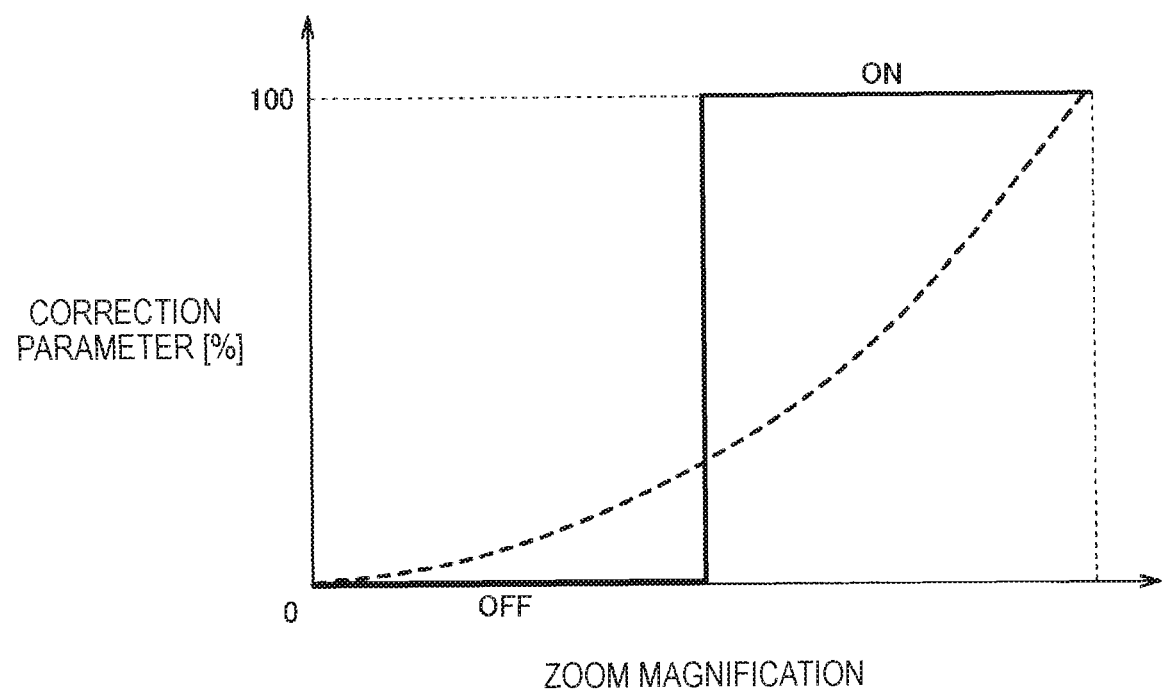
FIG. 15 is a property diagram illustrating a relationship between a zoom magnification and a correction gain.

FIG. 14 is a schematic diagram illustrating a configuration example of a case of performing electronic zoom after blurring correction. In the configuration illustrated in FIG. 14, an electronic zoom 1140, a correction gain decision unit 1142, a user interface (UI) 1144, and the gain adjustment unit 1123 are provided in addition to the configuration in FIG. 4B. The correction gain decision unit 1142 decides a correction gain in accordance with a zoom magnification of the electronic zoom 1140. FIG. 15 is a property diagram illustrating a relationship between a zoom magnification and a correction gain. The correction gain decision unit 1142 decides a correction gain on the basis of FIG. 15. As illustrated in FIG. 15, as a zoom magnification becomes larger, a value of a correction gain increases.

Because the subject is magnified more as a zoom magnification becomes larger, the distortion of the image that is caused by the shake of the endoscope 2 becomes larger. Thus, by increasing a correction gain as a zoom magnification becomes larger, it becomes possible to optimally correct blurring. Note that, gain adjustment may be consecutively performed as indicated by a broken line in FIG. 15, or on/off may be controlled by discretely changing a correction gain as indicated by a solid line in FIG. 15. Note that, the focus lens position acquisition unit 1120, the spatial frequency analysis unit 1124, the distance information detection unit 1128, and the electronic zoom 1140 that have been described above correspond to a distance-related parameter acquisition unit that acquires a distance-related parameter related to a distance to the subject.

6. Application to Microscopic Device

Figure 16:
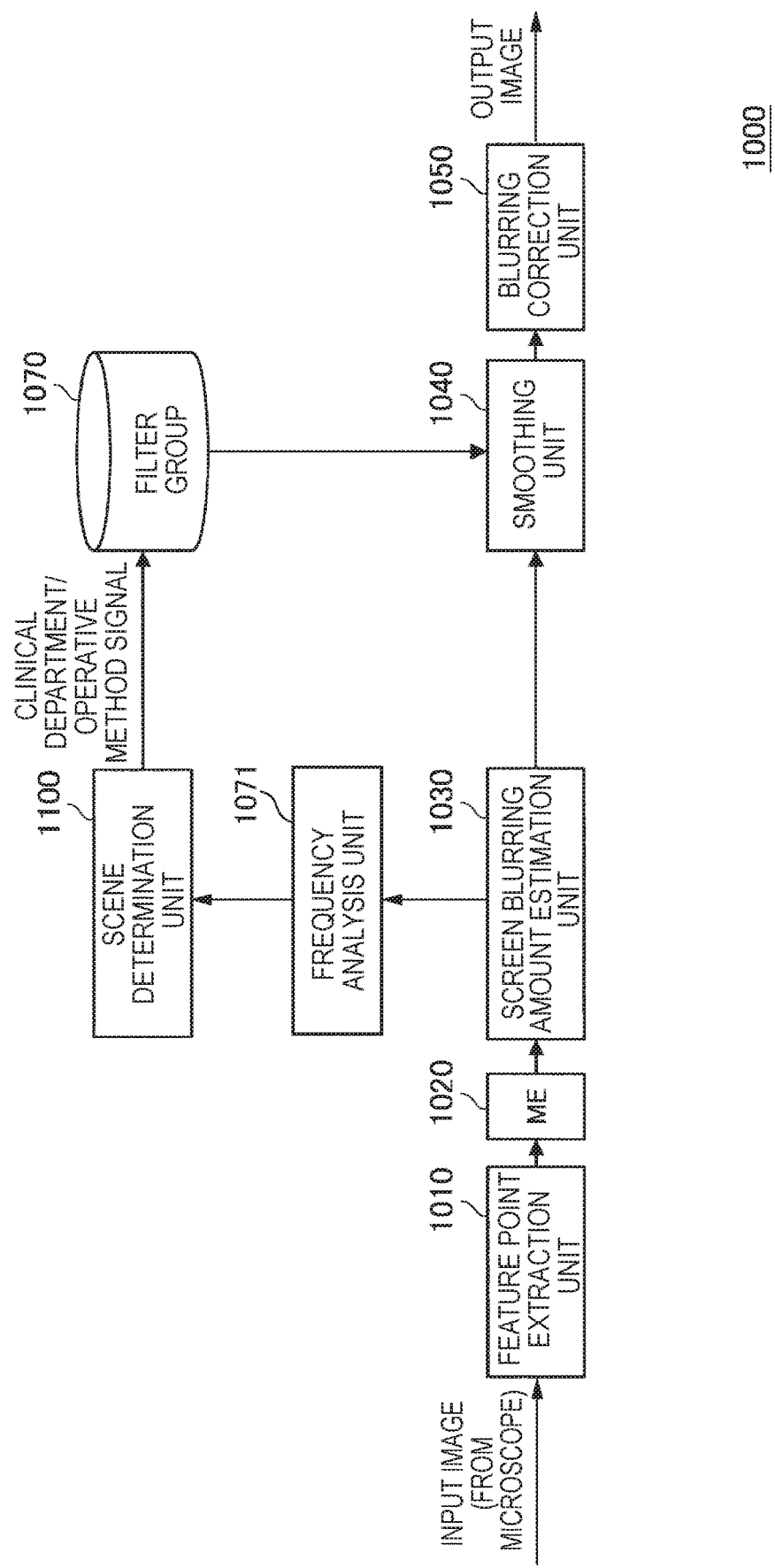
FIG. 16 is a schematic diagram illustrating a configuration example of performing blurring correction for an operative microscope.

FIG. 16 is a schematic diagram illustrating a configuration example of performing blurring correction of an image captured by a microscopic device (operative microscope). In the above-described examples, the description has been given of blurring correction of an image captured by the endoscope 2. Alternatively, the blurring correction can be similarly applied to an image captured by a microscopic device. The configuration illustrated in FIG. 16 is similar to FIG. 4A except that an input image is a microscopic image. The microscopic device generally includes a microscopic portion for enlarging and observing an observation target (operated portion of a patient), an arm portion that supports the microscopic portion at a distal end, and a base portion that supports a proximal end of the arm portion. The microscopic portion is an electronic image-capturing-type microscopic portion (so-called video-type microscopic portion) that electrically captures a captured image by an imaging apparatus (image sensor). In the case of operation that uses the microscopic device, in some cases, difficulty is felt in seeing a video-shot image due to the shake of a building or an arm. Thus, for example, at the time of craniotomy operation in cranial nerve surgery, similarly to the case of the endoscope 2, the feature point extraction unit 1010 extracts a feature point from an input image, the motion vector extraction unit 1020 performs motion vector detection for each feature point, and the image burring amount estimation unit 1030 estimates a blurring amount of the entire image. Then, the smoothing unit 1040 accumulates blurring amounts in the time direction, and performs smoothing by applying a filter. The blurring correction unit 1050 performs blurring correction on the smoothed blurring amounts. The correction of blurring caused by the vibration of a building or an arm can be thereby performed. Also in the operative microscope, "blurring" desired to be suppressed and "blurring" undesired to be suppressed are assumed. As indicated in Table 2, the "blurring" desired to be suppressed corresponds to a frequency of about 0 to 1 [Hz] and a frequency of about 8 to 9 [Hz]. In addition, the "blurring" undesired to be suppressed corresponds to a frequency of about 0 or 1 to 8, or 9 [Hz].

Figure 17:
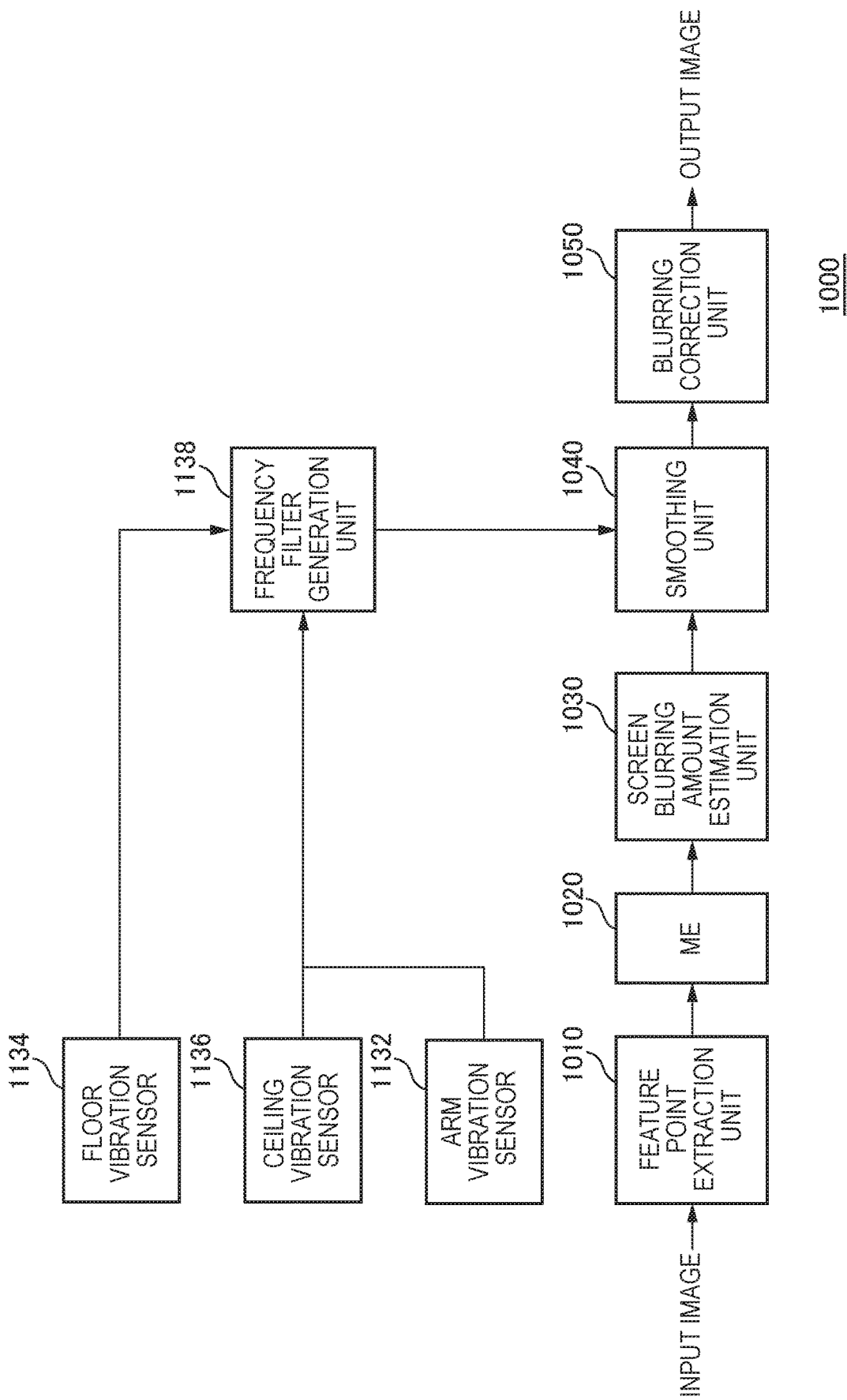
FIG. 17 is a schematic diagram illustrating an example in which the configuration in FIG. 16 is provided with a frequency filter for suppressing each eigen vibration component using vibration information from each sensor, as an input.
Figure 18:
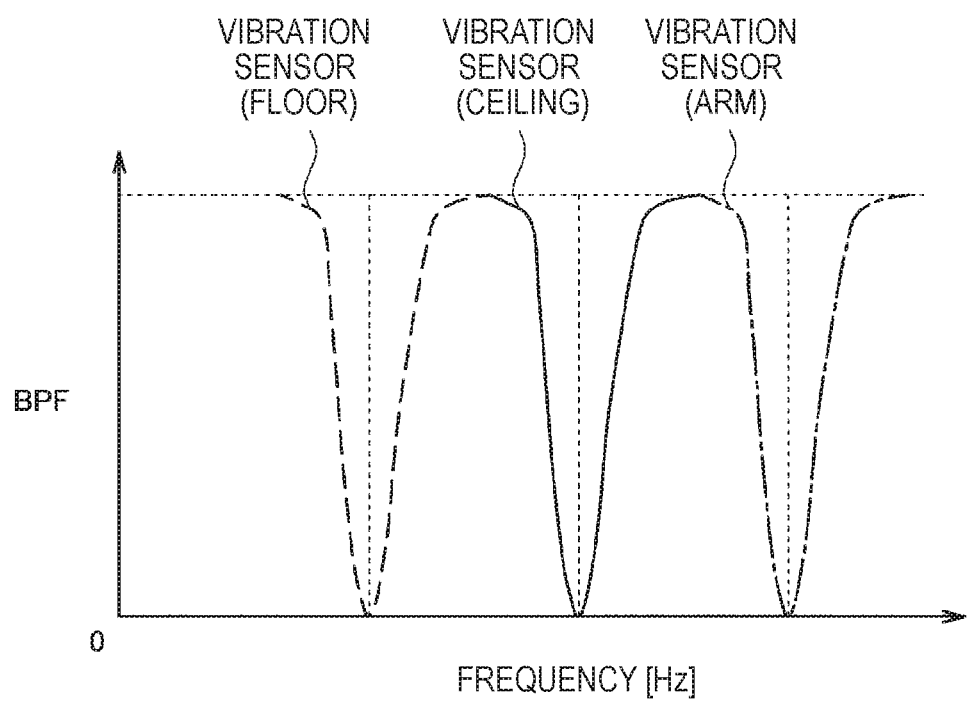
FIG. 18 is a schematic diagram illustrating a property of the frequency filter.

In blurring correction for the microscopic device, for performing blurring correction with higher accuracy, an arm vibration sensor 1132 is installed on an arm. Additionally, for detecting the vibration of a building, a floor vibration sensor 1134 is installed on a floor, and a ceiling vibration sensor 1136 is installed on a ceiling. FIG. 17 is a schematic diagram illustrating an example in which the configuration in FIG. 16 is provided with a frequency filter generation unit 1138 that generates a frequency filter for suppressing each eigen vibration component, using vibration information from each sensor, as an input. In addition, FIG. 18 is a schematic diagram illustrating a property of a frequency filter 1138 (bandpass filter). By the smoothing unit 104 performing smoothing processing using the frequency filter 1138 illustrated in FIG. 18, it is possible to set eigen vibration components of arm vibration, floor vibration, and ceiling vibration that are respectively detected by the arm vibration sensor 1132, the floor vibration sensor 1134, and the ceiling vibration sensor 1136, as targets of blurring correction to be performed by the blurring correction unit 1050, and suppress blurring caused by these.

FIG. 19 is a schematic diagram illustrating a configuration example of a case of obtaining a noise reduction (NR) effect on a moving image, by performing smoothing in a time direction filter according to the present embodiment. In the configuration example illustrated in FIG. 19, a frame position correction unit 1145 and a frame addition unit 1146 are added in addition to the configuration in FIG. 4B. Similarly to FIG. 4B, a color distribution and a spatial frequency distribution are extracted from an input image, a filter is selected after scene determination is performed, and smoothing is performed. By a frame position correction unit 1144 performing position correction on each frame, and the frame addition unit 1146 adding each frame, the noise reduction effect can be obtained on the moving image.

As described above, according to the present embodiment, because blurring correction is performed in accordance with a situation on the basis of a clinical department or a scene suitable for an operative method, blurring correction can be performed without removing a screen motion caused by a biological body motion. It therefore becomes possible to provide an optimum medical image suitable for a situation.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
    An image processing apparatus including:
        a blurring amount estimation unit configured to estimate a blurring amount of a medical image including a biological body motion of a subject; and
        a blurring correction processing unit configured to perform blurring correction processing so as not to remove a screen motion caused by the biological body motion, on a basis of the blurring amount.

(2)
    The image processing apparatus according to (1),
    in which the blurring correction processing unit includes
        a smoothing unit configured to smooth the blurring amount by accumulating the blurring amount in a time direction, and
        a blurring correction unit configured to perform blurring correction on a basis of the smoothed blurring amount, and
    the blurring correction processing unit performs the blurring correction processing in accordance with a situation, by changing a smoothing filter for the smoothing.

(3)
    The image processing apparatus according to (2), in which the blurring correction processing unit performs the blurring correction processing in accordance with a situation in which operation is being performed, an operative method of the operation, or a clinical department.

(4)
    The image processing apparatus according to (2), in which the blurring correction processing unit performs the blurring correction processing in accordance with a user instruction.

(5)
    The image processing apparatus according to (2), including
        a frequency analysis unit configured to perform frequency analysis of the blurring amount, in which the blurring correction processing unit performs the blurring correction processing on a basis of a result of the frequency analysis.

(6)
The image processing apparatus according to (2), including
a color distribution extraction unit configured to extract a color distribution of a medical image,
in which the blurring correction processing unit performs the blurring correction processing on a basis of the color distribution.

(7)
The image processing apparatus according to (2), including
a spatial frequency distribution extraction unit configured to extract a spatial frequency distribution of a medical image,
in which the blurring correction processing unit performs the blurring correction processing on a basis of the spatial frequency distribution.

(8)
The image processing apparatus according to (2), including
a mask diameter detection unit configured to detect a mask diameter of a medical image, in which the blurring correction processing unit performs the blurring correction processing on a basis of the mask diameter.

(9)
The image processing apparatus according to (2), including
a trocar presence/absence detection unit configured to detect presence or absence of use of a trocar in operation,
in which the blurring correction processing unit performs the blurring correction processing on a basis of the presence or absence of the use of the trocar.

(10)
The image processing apparatus according to any one of (1) to (9), further including:
a distance-related parameter acquisition unit configured to acquire a distance-related parameter related to a distance to a subject; and
a gain adjustment unit configured to adjust a gain of the blurring correction processing on a basis of the distance-related parameter.

(11)
The image processing apparatus according to (10), in which the gain adjustment unit increases the gain as a distance to a subject becomes larger.

(12)
The image processing apparatus according to (10), in which the distance-related parameter is focus lens position information, a spatial frequency of a subject, disparity in a stereo image, or a zoom magnification.

(13)
The image processing apparatus according to any one of (1) to (12), including:
a feature point extraction unit configured to extract a feature point from the medical image; and
a motion vector extraction unit configured to extract a motion vector from the feature point,
in which the blurring amount estimation unit estimates the blurring amount on a basis of the motion vector.

(14)
The image processing apparatus according to (13), in which, on a basis of a mask diameter of the medical image, the feature point extraction unit extracts the feature point from a narrower range in a mask as the mask diameter becomes smaller.

(15)
The image processing apparatus according to (2), in which the medical image is an endoscopic image or a microscopic image.

(16)
The image processing apparatus according to (15), in which the medical image is a microscopic image, and the image processing apparatus includes a filter generation unit configured to generate the smoothing filter for removing blurring caused by external vibration.

(17)
The image processing apparatus according to (16), in which the filter generation unit generates the smoothing filter on a basis of a detection value of a sensor configured to detect the external vibration.

(18)
An image processing method including:
estimating a blurring amount of a medical image including a biological body motion of a subject; and
performing blurring correction processing so as not to remove a screen motion caused by the biological body motion, on a basis of the blurring amount.

(19)
A medical system including:
an imaging apparatus configured to capture a medical image including a biological body motion of a subject; and
an image processing apparatus including
a blurring amount estimation unit configured to estimate a blurring amount of the medical image, and
a blurring correction processing unit configured to perform blurring correction processing so as not to remove a screen motion caused by the biological body motion, on a basis of the blurring amount.

REFERENCE SIGNS LIST 1030 screen blurring amount estimation unit
1040 smoothing unit
1050 blurring correction unit
1071 frequency analysis unit
1110 color distribution extraction unit
1112 spatial frequency distribution extraction unit
1114 mask diameter detection unit
1116 trocar presence/absence detection unit
1120 focus lens position acquisition unit
1124 spatial frequency analysis unit
1128 distance information detection unit

The invention claimed is:
1. An image processing apparatus, comprising:
circuitry configured to:
estimate a blurring amount of a medical image including a biological body motion of a subject;
perform, based on the estimated blurring amount, a blurring correction process so as not to remove a screen motion caused by the biological body motion,
acquire a distance between the image processing apparatus and the subject; and
adjust a gain of the blurring correction process based on the distance between the image processing apparatus and the subject, wherein the adjustment includes an increase of the gain of the blurring correction process based on an increase in the distance between the image processing apparatus and the subject.

2. The image processing apparatus according to claim 1, wherein the circuitry is further configured to:
   accumulate the estimated blurring amount in a time direction;
   select a smoothing filter;
   smooth the accumulated blurring amount by application of the selected smoothing filter; and
   perform the blurring correction process on the smoothed blurring amount.

3. The image processing apparatus according to claim 2, wherein the circuitry is further configured to: at least one of an operative method of an operation or a clinical department related to the operation based on the medical image; and
   select the smoothing filter based on the determined information.

4. The image processing apparatus according to claim 2, wherein the circuitry is further configured to:
   select an operative mode of an operation based on a user instruction; and
   select the smoothing filter based on the selected operative mode of the operation.

5. The image processing apparatus according to claim 2, wherein the circuitry is further configured to:
   perform frequency analysis of the estimated blurring amount;
   determine information including at least one of an operative method of an operation or a clinical department related to the operation based on a result of the frequency analysis; and
   select the smoothing filter based on the determined information.

6. The image processing apparatus according to claim 2, wherein the circuitry is further configured to:
   extract a color distribution of the medical image;
   determine information including at least one of an operative method of an operation or a clinical department related to the operation based on the color distribution; and
   select the smoothing filter based on the determined information.

7. The image processing apparatus according to claim 2, wherein the circuitry is further configured to:
   extract a spatial frequency distribution of the medical image;
   determine information including at least one of an operative method of an operation or a clinical department related to the operation based on the spatial frequency distribution; and
   select the smoothing filter based on the determined information.

8. The image processing apparatus according to claim 2, wherein the circuitry is further configured to:
   detect a mask diameter of the medical image;
   determine information including at least one of an operative method of an operation or a clinical department related to the operation based on the detected mask diameter; and
   select the smoothing filter based on the determined information.

9. The image processing apparatus according to claim 2, wherein the circuitry is further configured to:
   detect one of presence or absence of use of a trocar in an operation based on the estimated blurring amount of the medical image; based on the detected one of the presence or absence of the use of the trocar; and
   select the smoothing filter based on the determined information.

10. The image processing apparatus according to claim 1, wherein the circuitry is further configured to acquire a distance-related parameter associated with the distance between the image processing apparatus and the subject, and the distance-related parameter includes at least one of focus lens position information, a spatial frequency of the subject, disparity in a stereo image, or a zoom magnification.

11. The image processing apparatus according to claim 1, wherein the circuitry is further configured to:
    extract a feature point from the medical image;
    extract a motion vector from the feature point; and
    estimate the blurring amount based on the motion vector.

12. The image processing apparatus according to claim 11, wherein the circuitry is further configured to:
    detect a mask diameter of a mask of the medical image; and
    extract the feature point from a narrower range of the mask based on the detected mask diameter of the medical image.

13. The image processing apparatus according to claim 2, wherein the medical image is one of an endoscopic image or a microscopic image.

14. The image processing apparatus according to claim 13, wherein
    the medical image is the microscopic image, and
    the circuitry is further configured to generate the smoothing filter to remove blurring caused by external vibration.

15. The image processing apparatus according to claim 14, wherein the circuitry is further configured to generate the smoothing filter based on a detection value of a sensor configured to detect the external vibration.

16. An image processing method, comprising:
    in an image processing apparatus:
    estimating, a blurring amount of a medical image including a biological body motion of a subject;
    performing, based on the estimated blurring amount, a blurring correction process so as not to remove a screen motion caused by the biological body motion;
    acquiring a distance between the image processing apparatus and the subject; and
    adjusting a gain of the blurring correction process based on the distance between the image processing apparatus and the subject, wherein the adjustment inclues an increase of the gain of the blurring correction process based on an increase in the distance between the image processing apparatus and the subject.

17. A medical system, comprising:
    an imaging apparatus configured to capture a medical image including a biological body motion of a subject; and
    an image processing apparatus that includes circuitry configured to:
      estimate a blurring amount of the medical image;
      perform, based on the estimated blurring amount, a blurring correction process so as not to remove a screen motion caused by the biological body motion;
      acquire a distance between the image processing apparatus and the subject; and
      adjust a gain of the blurring correction process based on the distance between the image processing apparatus and the subject, wherein the adjustment includes an increase of the gain of the blurring correction process based on an increase in the distance between the image processing apparatus and the subject.

18. The image processing apparatus according to claim 1, wherein, in a case of an execution of an electronic zoom process, the circuitry is further configured to adjust the gain of the blurring correction process based on a zoom magnification of the electronic zoom process.

19. The image processing apparatus according to claim 1, wherein the circuitry is further configured to detect the distance between the image processing apparatus and the subject based on a disparity of a stereo image of the subject.

* * * * *